US012799480B2

(12) United States Patent
Wang et al.

(10) Patent No.: US 12,799,480 B2
(45) Date of Patent: Nov. 17, 2026

(54) METHOD FOR MULTI-DIMENSIONAL ANALYSIS OF CELL EPIGENOMICS

(71) Applicant: BGI SHENZHEN, Shenzhen (CN)

(72) Inventors: Chunqing Wang, Shenzhen (CN); Liang Wu, Shenzhen (CN); Zihao Li, Shenzhen (CN); Yu Zhong, Shenzhen (CN); Yaling Huang, Shenzhen (CN); Yue Yuan, Shenzhen (CN); Chuanyu Liu, Shenzhen (CN)

(73) Assignee: BGI SHENZHEN, Shenzhen (CN)

( * ) Notice: Subject to any disclaimer, the term of this patent is extended or adjusted under 35 U.S.C. 154(b) by 858 days.

(21) Appl. No.: 18/026,110

(22) PCT Filed: Sep. 16, 2020

(86) PCT No.: PCT/CN2020/115499
§ 371 (c)(1),
(2) Date: Mar. 13, 2023

(87) PCT Pub. No.: WO2022/056704
PCT Pub. Date: Mar. 24, 2022

(65) Prior Publication Data
US 2024/0018512 A1 Jan. 18, 2024

(51) Int. Cl.
*C12N 15/10* (2006.01)

(52) U.S. Cl.
CPC ..... *C12N 15/1082* (2013.01); *C12N 15/1065* (2013.01)

(58) Field of Classification Search
CPC ........................................................ C12Q 1/68
See application file for complete search history.

(56) References Cited

U.S. PATENT DOCUMENTS

2016/0060691 A1 3/2016 Giresi et al.
2018/0237951 A1 8/2018 Bock et al.
2022/0214356 A1* 7/2022 Henikoff .............. C12Q 1/6804

FOREIGN PATENT DOCUMENTS

CA 3113271 A1 4/2020
CN 206417031 U 8/2017
(Continued)

OTHER PUBLICATIONS

Notice of Reasons for Rejection for Chinese Patent Application No. 202080098209.X, dated Jun. 1, 2024, with machine English translation.
(Continued)

*Primary Examiner* — Yung-Sheng M Tsui
(74) *Attorney, Agent, or Firm* — Westman, Champlin & Koehler, P.A.; Z. Peter Sawicki

(57) ABSTRACT

A method for analyzing cell epigenomics from multiple dimensions. The method comprises the following steps: by using ChiTag transposase and conventional Tn5 transposase in cells, respectively embedding different linker sequences, and achieving common analysis of information of a chromatin open region and information of a specific protein binding sequence on a cellular level. The method has important application prospects in aspects such as study of development and/or disease related cell population heterogeneity, drawing of a cell map, analysis of tumor cells having different clinical characteristics, and clinical study of evolution and/or metastasis of tumor cells.

20 Claims, 7 Drawing Sheets

Specification includes a Sequence Listing.

(56) References Cited

FOREIGN PATENT DOCUMENTS

| | | | |
|---|---|---|---|
| CN | 108360074 | A | 8/2018 |
| CN | 108368540 | A | 8/2018 |
| CN | 111154835 | A | 5/2020 |
| WO | 2019184044 | A1 | 10/2019 |
| WO | 2020009665 | A1 | 1/2020 |

OTHER PUBLICATIONS

International Search Report for EP Application 20953564.0, date of mailing Jun. 6, 2024, 11 pages.
Overview of the Technology of Single Cell Sequencing, Quan et al., Chinese Journal of Medicinal Guide, Jul. 22, 2020, vol. 22 No. 7, 7 pages.
Written Opinion for International Application for PCT/CN/2020/115499, date of mailing Jun. 16, 2021, 3 pages.
Buenrostro, Jason et. al., ATAC-Seq: A Method for Assaying Chromatin Accessibility Genome-Wide, Curr Protoc Mol Biol, Jan. 5, 2016, 109: 21.29.1-21.29.9, doi: 10.1002/0471142727.mb2129s109, 10 pages.
Kaya-Okur, Hatice S. et al., Cut&Tag for Efficient Epigenomic Profiling of Small Samples and Single Cells, Nature Communications, 2019, 10:1930| https://doi.org/10.1038/s41467-019-09982-5|www.nature.com/naturecommunications, 10 pages.
Kaya-Okur, H. S. et al. "Cut&Tag for efficient epigenomic profiling of small samples and single cells" Nature Communications (2019) vol. 10, Article No. 1930, pp. 1-10.
Buenrostro, J. et al. "ATAC-seq: A Method for Assaying Chromatin Accessibility Genome-Wide" Current Protocols in Molecular Biology (2015); 109:21.29.1-21.29.9.
Kaya-Okur, H. S. et al. "Efficient low-cost chromatin profiling with Cut&Tag" Nature Protocols (2020) 15(10): 3264-3283.
Lhoumaud, P. et al. "EpiMethylTag: simultaneous detection of ATAC-seq or ChIP-seq signals with DNA methylation" Genome Biology (2019) vol. 20, Article No. 248, pp. 1-12.
International Search Report issued for PCT/CN2020/115499, dated Jun. 16, 2021.
Written Opinion of the International Searching Authority issued for PCT/CN2020/115499, dated Jun. 16, 2021.

* cited by examiner

METHOD FOR MULTI-DIMENSIONAL ANALYSIS OF CELL EPIGENOMICS

CROSS-REFERENCE TO RELATED APPLICATION

This Application is a Section 371 National Stage Application of International Application No. PCT/CN2020/115499, filed Sep. 16, 2020 and published as WO2022/056704 on Mar. 24, 2022, in Chinese, the contents of which are hereby incorporated by reference in their entirety.

FIELD

The present disclosure relates to the field of bioinformatics, specifically to a method for multi-dimensional analysis of cell epigenomics.

BACKGROUND

The technology of epigenomics is an important tool for analyzing epigenomics. Compared with the technology that can only describe average epigenome characteristics of the whole cell population, epigenome is becoming a new technology for studying a plasticity and heterogeneity of cells. At present, many technologies of epigenomics have been developed to describe the epigenome of a heterogenic tumor tissue at single-cellular and multi-cellular levels.

CUT&Tag technology utilizes a ChiTag enzyme to interrupt a DNA near a target protein specifically and connect an adapter to a DNA fragment, subsequently utilizes the adapter of the ChiTag enzyme for amplifying thereby obtaining a specific protein-DNA interacted library for high-throughput sequencing. A schematic diagram of a CUT&Tag method is shown in FIG. 1, referring to //doi.org/10.1038/s41467-019-09982-5.

ATAC-seq technology utilizes a conventional Tn5 transposase to interrupt a DNA of an accessible-chromatin region and connects an adapter to a DNA fragment, subsequently utilizes the adapter of the Tn5 transposase for amplifying thereby obtaining a DNA library of the accessible-chromatin region for high-throughput sequencing. A schematic diagram of an ATAC-seq method is shown in FIG. 2, referring to doi: 10.1002/047142727mb2129s109.

At present, although the CUT&Tag and the ATAC-seq are relatively mature, neither of them can co-analyze information of a target protein-DNA interaction and the accessible-chromatin region of a same cell.

SUMMARY

Problems to be solved by the present disclosure are: 1) capturing information of a DNA sequence interacted with a target protein and an accessible-chromatin region simultaneously; and 2) performing a high-throughput DNA library construction with an idrop platform.

In a first aspect, the present disclosure provides in embodiments a method for multi-dimensional analysis of cell epigenomics.

The method for multi-dimensional analysis of cell epigenomics provided by embodiments of the present disclosure may include the following steps: utilizing a ChiTag transposase and a Tn5 transposase to respectively embed different adapter sequences in a cell; and performing a co-analysis for information of an accessible-chromatin region and a target-protein binding sequence at the cellular level.

The method may be a method A or a method B.

The method A is a method for multi-dimensional analysis of a single cell epigenomics, and may include the following steps:

(A1) changing the permeability of a cell to be tested;

(A2) adding an antibody (i.e. a first antibody) corresponding to the target protein to the cell after the treatment of the step (A1) for incubation;

(A3) adding a secondary antibody (i.e., an antibody anti the antibody corresponding to the target protein) to the cell after the treatment of the step (A2) for incubation;

(A4) adding the ChiTag transposase to the cell after the treatment of the step (A3) for incubation;

(A5) adding a reaction reagent to the cell after the treatment of the step (A4) for incubation, and adding a conventional Tn5 transposase after the incubation, which achieves a DNA fragment;

(A6) generating a droplet including a single cell with a water-in-oil structure such as performed by a DNBelab C4 portable single cell system, and performing an amplification within the droplet after the reaction of the step (A5);

(A7) performing a demulsification, amplification and purification;

(A8) performing an enzyme digestion to obtain a final library; and (A9) performing high-throughput sequencing on the final library obtained in the step (A8) to analyze the information of the accessible-chromatin region and the specific target protein binding sequence at a single cellular level.

The method B is a method for multi-dimensional analysis of multi-cell epigenomics, and may include the following steps:

(B1) changing the permeability of a cell to be tested;

(B2) adding an antibody corresponding to the target protein to the cell after the treatment of the step (B1) for incubation;

(B3) adding a secondary antibody to the cell after the treatment of the step (B2) for incubation;

(B4) adding the ChiTag transposase to the cell after the treatment of the step (B3) for incubation;

(B5) adding a reaction reagent to the cell after the treatment of the step (B4) for incubation, and adding a conventional Tn5 transposase after the incubation;

(B6) performing an amplification and purification;

(B7) performing an enzyme digestion to obtaining a final library; and (B8) performing high-throughput sequencing on the final library obtained in the step (B7) to analyze the information of the accessible-chromatin region and the target-protein binding sequence at a multiple cellular level.

Each of the steps (A1) and (B1) may further include the following steps of a pretreatment to the cell to be tested before changing the permeability of the cell to be tested: after collecting the cell, performing a centrifugation at 600 g for 3 min and discarding the supernatant; and resuspending the cells with at least one time of volume of a basic wash buffer (Wash Buffer), followed by a centrifugation at 600 g for 3 min, and discarding the supernatant. All operations here are carried out at room temperature (23-28 °C, the same below) to minimize the pressure on cells.

In the steps (A1) and (B1), changing the permeability of the cell to be tested may be achieved by resuspending the cell to be tested in a NP40-digoxin wash buffer.

Further, each of the steps (A1) and (B1) includes: resuspending 500,000 to 1,000,000 cells in 1 ml of the NP40-digoxin wash buffer (namely a first resuspension); centrifuging at 600 g for 3 min and discarding the supernatant; and resuspending the cells by adding 49 μl of the NP40-digoxin wash buffer containing 1.5-2.5 mM (e.g. 2 mM) EDTA (namely a second resuspension).

The NP40-digoxin wash buffer (NP4O-Digitonin Wash Buffer) is obtained by additionally adding 0.01% (volume percentage) NP40 and 0.01% digoxin to a basic wash buffer (Wash Buffer).

In an embodiment of the disclosure, the digoxin is BN2006 #Digitonin (5%)/brand&Invitrogen/specification&1, and its weight % is 5. The concentration of digoxin in the NP40-digoxin wash buffer is equal to the concentration of digoxin in this product with 500 times dilution.

The basic wash buffer above consists of: 20 mM HEPES in pH 7.5, 150 mM NaCl, 0.5 mM spermidine, and 1× protease inhibitor (Protease inhibitor cocktail, Sigma-Aldrich, Cat. No. 11873580001).

In the steps (A2) and (B2), the antibody (i.e. the first antibody) corresponding to the target protein is directly added to a cell resuspension at the second resuspension obtained in the steps (A1) and (B1).

The proportion of the first antibody added in this step is about: adding 1 μL of the first antibody to every 49 μL of the cell resuspension.

In specific embodiments of the disclosure, in steps (A2) and (B2), the antibody (i.e. the first antibody) corresponding to the target protein is H3K27me3 antibody. Accordingly, the secondary antibody is an antibody anti the H3K27me3 antibody.

In steps (A2) and (B2) of the method, the incubation may be performed at room temperature for 2 h or at 4 °C for overnight (i.e., 10-12 h, the same below).

Each of the steps (A3) and (B3) of the method may further include steps of washing and centrifugation before adding the secondary antibody, in which the washing may be performed with the NP40 digoxin wash buffer described above, and the centrifugation may be performed at 600 g for 3 min.

In specific embodiments of the disclosure, the centrifugation and the washing are performed alternately in sequence, with a total of one washing and one centrifugation, and the supernatant is discarded after the centrifugation.

After the centrifugation, the method further includes a step of resuspending the cells by adding the NP40-digoxin wash buffer to the precipitation.

Specifically, the resuspension in that step may be for resuspending about 500,000 to 1,000,000 cells by 98 μl of the NP40-digoxin wash buffer above.

In the steps (A3) and (B3) of the method, the secondary antibody may be added to the cell resuspension obtained in that step.

The proportion of the secondary antibody added is about: adding 1-2 μL (e.g. 2 μL) of the secondary antibody to every 98 μL of the cell resuspension.

In the steps (A3) and (B3) of the method, the incubation may be performed at room temperature for 30 min.

Each of the steps (A3) and (B3) of the method may further include steps of washing and centrifugation after the incubation, in which the centrifugation may be performed at 600 g for 3 min, and the washing may be performed with the NP40-digoxin wash buffer above.

In specific embodiments of the disclosure, the centrifugation and the washing are performed alternately in sequence, with a total of three times washing and three times centrifugation (i.e., the times of centrifugation equal to the washing times), and the supernatant is discarded after every centrifugation.

Each of the steps (A4) and (B4) of the method may further include steps of centrifugation and cell resuspension sequentially before adding the ChiTag transposase, in which the centrifugation is performed at 600 g for 3 min, and the cell resuspension is performed by resuspending the cell with a NP4O-Dig-med-buffer (i.e., a chitag enzyme incubation buffer).

The NP4O-Dig-med-buffer (i.e., the chitag enzyme incubation buffer) consists of: 0.01% (volume percentage) NP40; 0.01% digoxin, 20 mM HEPES in pH 7.5; 300 mM NaCl; 0.5 mM spermidine and 1× protease inhibitor (Protease inhibitor cocktail, Sigma-Aldrich, Cat. No. 11873580001).

The ratio for resuspending the cell is about: resuspending 50,000 cells by adding the NP4O-Dig-med-buffer to 99 μL.

In each of the steps (A4) and (B4) of the method, a PrimerA, a ChIP-Tn5-PrimerB and a ChIP-Tn5-PrimerC are further added while adding the ChiTag transposase.

The PrimerA is a single strand DNA shown in SEQ ID NO. 1 modified with a phosphate group at the 5' end, the ChIP-Tn5-PrimerB is a mixture of four single strand DNAs as shown in SEQ ID NO. 2, SEQ ID NO. 3, SEQ ID NO. 4 and SEQ ID NO. 5, and the ChIP-Tn5-PrimerC is a mixture of four single strand DNAs as shown in SEQ ID NO. 6, SEQ ID NO. 7, SEQ ID NO. 8 and SEQ ID NO. 9.

In steps (A4) and (B4) of the method, the ChiTag transposase may be added to the resuspended cell suspension.

The ratio for adding the ChiTag transposase is about adding 99 μL of the cell suspension to 1 μL of a pA-Tn5 adapter complex, in which the pA-Tn5 adapter complex is obtained by evenly mixing the ChiTag transposase with a ChIP double strand adapter mixture at a molar ratio of 1:1, and incubating them at 25 °C for 1 h, where a final concentration of the ChiTag transposase in the pA-Tn5 adapter complex is 5.75 pmol/μl, and the ChIP double strand adapter mixture includes the PrimerA, the ChIP-Tn5-PrimerB and the ChIP-Tn5-PrimerC.

Further, the ChIP double strand adapter mixture may be prepared according to a method including the following steps: at step 1, preparing the following reaction systems by: for a reaction system I, mixing the Primer A and the ChiP-Tn5-PrimerB in an equimolar manner, such as mixing 10 μl of the Primer A (100 μM) with 10 μl of the ChIP-Tn5-PrimerB (100 μM, the final concentration of each primer is 25 μM); for Reaction system II, mixing the Primer A and the ChIP-Tn5-PrimerC in an equimolar manner, such as mixing 10 μl of the Primer A (100 μM) with 10 μl of the ChIP-Tn5-PrimerC (100 μM, the final concentration of each primer is 25 μM); at step 2, subjecting the reaction system I and the reaction system II individually to the following reaction procedure of 75 °C for 15 min; 60 °C for 10 min; 50 °C for 10 min; 40 °C for 10 min; and 25 °C for 30 min, with a lid temperature of 105 °C; and at step 3, mixing the reaction system I and the reaction system II in an equimolar manner after the reaction procedure so as to obtain the ChIP double strand adapter mixture.

In the steps (A4) and (B4) of the method, the incubation may be performed at room temperature for 1 h.

The steps (A4) and (B4) of the method may further include steps of washing and centrifugation after the incubation, in which the centrifugation may be performed at 300 g for 3 min, and the washing may be performed with the NP4O-Dig-med-buffer (i.e. the chitag enzyme incubation buffer) above.

In specific embodiments of the disclosure, the centrifugation and the washing are performed alternately in sequence, with a total of three times of washing and four times of centrifugation, and the supernatant is discarded after every centrifugation.

In the steps (A5) and (B5) of the method, the reaction reagent may be directly added to the cell precipitation obtained after the last centrifugation in the step (A4).

In the steps (A5) and (B5) of the method, the reaction reagent may be a Tagmentation Buffer (i.e. a chitag enzyme breaking buffer).

The Tagmentation Buffer, i.e. the chitag enzyme breaking buffer, is obtained by adding 10 mM $MgCl_2$ to the NP4O-Dig-med-buffer (i.e. the chitag enzyme incubation buffer) above.

In the steps (A5) and (B5) of the method, the incubation may be performed at 37 °C for 60 min.

In the steps (A5) and (B5) of the method, an centrifugation at 300 g for 3 min after the incubation at 37 °C is performed, and the conventional Tn5 transposase is added and reacted at 37 °C with 500 rpm for 30 min.

In the steps (A5) and (B5) according to the method, the PrimerA, an ATAC-Tn5-primerB and an ATAC-Tn5-PrimerC are further added while adding the Tn5 transposase.

The Primer A is the single strand DNA shown in SEQ ID NO. 1 modified with a phosphate group at the 5' end, the ATAC-Tn5-primerB is a mixture of four single strand DNAs as shown in SEQ ID No. 10, SEQ ID No. 11, SEQ ID NO. 12 and SEQ ID NO. 13, and the ATAC-Tn5-PrimerC is a mixture of four single strand DNAs as shown in SEQ ID NO. 14, SEQ ID NO. 15, SEQ ID NO. 16 and SEQ ID NO. 17.

Further, the Tn5 transposase may be added in a form of an ATAC transposable reagent mixture, and per 25 μl of the ATAC transposable reagent mixture contains 5 μl of 5× TAG buffer (BGE005B01), 16 μl of PBS with 1% BSA (A0332), and 4 μl of a Tn5 adaptor complex, in which the Tn5 adaptor complex is obtained by evenly mixing the Tn5 transposase and a Tn5 double strand adapter mixture at a molar ratio of 1:1 and incubating them at 25 °C for 1 h, where a final concentration of the Tn5 transposase in the Tn5 adaptor complex is 0.875 U/μl, and the Tn5 double strand adapter mixture contains the PrimerA, the ATAC-Tn5-primerB and the ATAC-Tn5-PrimerC.

Further, the Tn5 double strand adapter mixture may be prepared according to a method including the following steps: at step 1, preparing the following reaction systems by: for a reaction system I, mixing the Primer A and the ATAC-Tn5-PrimerB in an equimolar manner such as the Primer A (100 μM) for 10 μl and the ATAC-Tn5-PrimerB (100 μM, the final concentration of each primer is 25 μM) for 100, and for a Reaction system II, mixing the Primer A and the ATAC-Tn5-PrimerC in an equimolar manner such as the Primer A (100 μM) for 10 μl and the ATAC-Tn5-PrimerC (100 μM), the final concentration of each primer is 25 μM) for 100; at step 2, subjecting the reaction system I and the reaction system II individually to the following reaction procedure of 75 °C for 15 min; 60 °C for 10 min; 50 °C for 10 min; 40 °C for 10 min; and 25 °C for 30 min, with a lid temperature of 105 °C; and at step 3, mixing the reaction system I and the reaction system II in an equimolar manner after the reaction procedure so as to obtain the Tn5 double strand adapter mixture.

Ratios for adding the reaction reagent (Tagmentation Buffer) and the ATAC transposable reagent mixture are about: adding 300 μL of the reaction reagent (Tagmentation Buffer) and/or 25 μL of the ATAC transposable reagent mixture for every 50,000 cell.

In the step (A6) of the method, generating a droplet including a single cell with a water-in-oil structure may specifically be a generation of a single cell with a water-in-oil structure by the BGI DNBelab C4 portable single cell system.

In the step (A6) of the method, primers for the amplification within the droplet include a Tn Primer and a 183+C Primer. The Tn Primer is a single strand DNA as shown in SEQ ID NO. 18, and the 183+C Primer is a single strand DNA as shown in SEQ ID NO. 19.

In specific embodiments of the disclosure, the reaction procedure for performing the amplification within the droplet is: 72 °C for 30 min; 98 °C for 30 s; 98 °C for 10 s, 63 °C for 30 s, 72 °C for 1 min, for 10 cycles; 72 °C for 5 min; and hold at 4 °C.

In the step (A7) of the method, the demulsification may be realized according to the following steps: transferring the droplet after the amplification in the step (A6) to a low adsorption centrifuge tube, adding an Additive B (Perfluoro-1-octnaol, A63881) and inverting and mixing them, then performing centrifugation at 1,000 g for 1 min, and statically placing the tube in a magnetic stand for 1 min to remove the liquid.

Further, the step (A7) of the method may include the following steps: adding a Wash Buffer F (formula: 10 ml of TE Buffer and 10 μL of 10% Tween-20, AM9820), inverting and mixing the mixture, then performing centrifugation at 1,000 g for 1 min, and placing the tube in a magnetic stand for 1 min to remove the supernatant. This step may be repeated once. After the supernatant is discarded, an ATAC Enzyme II treatment is performed with incubation in a metal bath with 1000 rpm at 37 °C for 45 min.

Further, the step (A7) may include the following steps after the enzyme treatment: instantaneously centrifuging, adding a Wash Buffer E (formula: 9.75 ml of TE Buffer and 0.25 ml of 20% SDS, AM9820), inverting and mixing them to stop the reaction; then performing centrifugation at 1,000 g for 1 min, and statically placing the tube in a magnetic stand for 1 min to remove the liquid.

Further, after that, the step (A7) may include a step of washing the magnetic beads as follows: adding the Wash Buffer F, inverting and mixing them, then performing centrifugation at 1,000 g for 1 min, and statically placing the tube in a magnetic stand for 1 min to remove the supernatant. This step may be repeated twice.

In the step (A7) of the method, primers for the amplification include the Tn Primer and a 183-pho Primer, in which the Tn Primer is the single strand DNA as shown in SEQ ID NO. 18, and the 183-pho Primer is a single strand DNA modified with a phosphate group at the 5' end as shown in SEQ ID NO. 20.

Further, the amplification may be performed as the following steps: after washing the magnetic beads and removing the supernatant, adding a PCR Ready Mix containing an ATAC Enzyme III (2× KAPA HiFi HotStart Ready Mix, KK2602), the Tn Primer, the 183-pho Primer, 60% Optiprep Density Gradient Medium (D1556-250ML) and NF—$H_2O$, mixing it with the magnetic beads well by blowing, and dividing them into an eight-tube strip evenly, washing the centrifuge tube again with the PCR Ready Mix, and dividing the PCR Ready Mix for the washing into the eight-tube strip evenly, which are operated at 4 °C to avoid inactivation of the PCR Ready Mix.

In specific embodiments of the disclosure, the reaction procedure for the amplification in the step (A7) is as follows:

98 °C for 30 s; 98 °C for 10 s, 63 °C for 30 s, 72 °C for 1 min, for cycles (e.g., 15 cycles); 72 °C for 5 min; and hold at 4 °C.

In the step (A7) of the method, the purification is performed by adding 1.2 volumes of the magnetic beads to a product of the amplification (namely purification with 1.2× magnetic beads).

In the step (A7) of the method, the magnetic beads may be AgencourtAMPure XP magnetic beads.

In the step (B6) of the method, primers for the amplification include a Bulk-N5 Primer and a 183+C-pho Primer, in which the Bulk-N5 Primer is a single strand DNA as shown in SEQ ID NO. 22, and the 183+C-pho Primer is a single strand DNA modified with a phosphate group at the 5' end as shown in SEQ ID NO. 23.

Further, the reaction procedure for the amplification is as the follows: 72 °C for 5 min; 98 °C for 30 s; 98 °C for 10 s, 63 °C for 30 s, 72 °C for 5 s, for 15 cycles; 72 °C for 1 min; and hold at 12 °C.

Each of the steps (A8) and (B7) may further include a cyclization before the enzyme digestion, where the cyclization may be further performed with a 153±181 Splint oligo.

The 153+181 splint oligo is a single strand DNA as shown in SEQ ID NO. 21.

Further, a thermal denaturation into a single strand is performed first, followed by the cyclization.

The 153+181 Splint oligo is added to a reaction system of the thermal denaturation into a single strand.

In specific embodiments of the disclosure, the reaction system of the thermal denaturation into a single strand is as follows: 200-400 ng of the purified DNA mixture, 3 μL of the 153+181 Splint oligo with a concentration of 20 μM, and NF—$H_2O$ for making up the volume to 50 μL.

In specific embodiments of the disclosure, a reaction condition of the thermal denaturation into a single strand is 95 °C for 3 min; and hold at 4 °C.

In specific embodiments of the disclosure, the reaction system of the cyclization is as follows: 50 μL of a product of the thermal denaturation into the single strand, 6 μL of 10× TA buffer (EPICENTRE TA6160), 0.6 μL of ATP with a concentration of 100 mM, 0.6 μL of T4 DNA ligase with a concentration of 400 U/μL, and 2.8 μL of TE Buffer.

In specific embodiments of the disclosure, a reaction condition of the cyclization is 37 °C for 45 min, and hold at 4 °C.

In the steps (A8) and (B7) of the method, an EXO I enzyme (NEB M0293L) and an EXO III enzyme (NEB M0206L) may be used for the enzyme digestion.

In the specific embodiment of the disclosure, a reaction system of the enzymatic digestion is as follows: 60 μL of a connected products obtained by the above cyclization; 0.4 μL of 10×TA buffer (EPICENTRE TA6160); 1.95 μL of the EXO I enzyme with a concentration of 20 U/μL; 0.65 μL of the EXO III enzyme with a concentration of 100 U/μL; and 1 μL of TE Buffer.

In specific embodiments of the disclosure, a reaction condition of the enzyme digestion is as follows: 37 °C for 30 min; and hold at 4 °C. After that, 4 μL of 0.1 mM EDTA (AMBION AM9260G) are added to stop the reaction.

Each of the steps (A8) and (B7) of the method may further include a purification for a product of the enzyme digestion with magnetic beads.

In the steps (A8) and (B7) of the method, the magnetic beads for the purification for the product of the enzyme digestion may be PEG32 beads.

Further, 90 μL of PEG32 beads are added to 64 μL of the product of the enzyme digestion above, and the following operations are performed: shaking by vertex to mix the mixture well, then incubating at room temperature for 10 minutes; separating the magnetic beads and the liquid by the magnetic stand; removing the supernatant after the solution is clarified; keeping the tube in the magnetic stand all the time, and adding 80% ethanol to wash the magnetic beads; removing the supernatant after incubation at room temperature for 30 seconds; keeping the tube in the magnetic stand all the time, opening a lid of the tube to dry the magnetic beads by the air for 3 minutes; taking the tube out of the magnetic stand and adding sterilized ultra-pure water for elution; mixing them well and separating the magnetic beads and a liquid in the tube in the magnetic stand; after the solution is clarified, removing the supernatant into a sterilized tube and store it at −20 °C. The result here is the final library.

In the steps (A9) and (B8) of the method, the sequencing is high-throughput sequencing. As an example, the high-throughput sequencing may be pair-end sequencing. As an example, the sequencing type may be PE50+26+10, i.e., pair-end sequencing, 50 bp for each end, 26 bp for barcode 1 sequence, and 10 bp for barcode 2 sequence.

In the method, the test cell may be a tumor cell K562.

In a second aspect, the present disclosure provides in embodiments a method for constructing a DNA library for multi-dimensional analysis of cell epigenomics.

The method for constructing a DNA library for multi-dimensional analysis of cell epigenomics provided in embodiments of the present disclosure may include steps (A1)-(A8) of the method A or steps (B1)-(B7) of the method B according to the first aspect above.

In the third aspect, the present disclosure provides in embodiments a kit.

The kit provided in embodiments of the present disclosure may include a ChiTag transposase, a conventional Tn5 transposase and other reagents related to CUT&Tag technology and/or ATAC-seq technology, and the kit is used for:

(B1) multi-dimensional analysis of cell epigenomics; or (B2) constructing a DNA library for multi-dimensional analysis of cell epigenomics.

Further, the other reagents related to the CUT&Tag technology and/or ATAC-seq technology may be selected from all or part of the followings: a NP40-digoxin wash buffer added with 1.5-2.5 mM (e.g. 2 mM) EDTA as provided above; a NP40-digoxin wash buffer as provided above; a basic wash buffer as provided above; an antibody corresponding to a target protein as provided above; a secondary antibody as provided above; a NP4O-Dig-med-buffer (i.e. chitag enzyme incubation buffer) as provided above; a Tagmentation Buffer (i.e. chitag enzyme breaking buffer) as provided above; a stop buffer (i.e. 4× stop buffer) as provided above; a PrimerA modified with a phosphate group at the 5' end shown in SEQ ID NO. 1 as provided above; a ATAC-Tn5-PrimerB shown in SEQ ID NOs. 10-13 as provided above; a ATAC-Tn5-PrimerC shown in SEQ ID NOs. 14-17 as provided above; a ChIP-Tn5-PrimerB shown in SEQ ID NOs. 2-5 as provided above; a ChIP-Tn5-PrimerC shown in SEQ ID NOs. 6-9 as provided above; a Tn Primer shown in SEQ ID NO. 18 as provided above; a 183+C Primer shown in SEQ ID NO. 19 as provided above; a 183-pho Primer modified with a phosphate group at the 5' end shown in SEQ ID NO. 20 as provided above; AgencourtAMPure XP magnetic beads; a Bulk N5 Primer shown in SEQ ID NO. 22 as provided above; a 183+C-pho Primer shown in SEQ ID NO. 23 as provided above; a 153+181 Splint oligo shown in SEQ ID NO. 21 as provided above; an EXO I enzyme; an EXO III enzyme; and PEG32 beads.

Further, the kit may further include a readable medium recording a method according to the first or second aspect of the present disclosure, for example, may be data storage devices such as paper, or optical disks or USB flash disks.

In a fourth aspect, the present disclosure provides in embodiments a system.

The system provided in embodiments of the present disclosure includes a kit described above, and an instrument and equipment related to CUT&Tag technology and/or ATAC-seq technology, and the system is used for:

(B1) multi-dimensional analysis of cell epigenomics; or (B2) constructing a DNA library for multi-dimensional analysis of cell epigenomics.

Further, the instrument and equipment related to the CUT&Tag technology and/or ATAC-seq technology may be selected from all or part of the followings: a high-throughput sequencer such as a BGISEQ500 sequencer; a PCR amplifier; a DNBelab C4 portable single cell system; a centrifuge; a shaker; a microscope; and a cell counting chamber.

In a fifth aspect, the present disclosure provides use of a kit or a system provided above in:

(B1) multi-dimensional analysis of cell epigenomics; or (B2) constructing a DNA library for multi-dimensional analysis of cell epigenomics.

In a sixth aspect, the present disclosure provides in embodiments use of a method, a kit or a system as provided above in any one of:

(C1) researching cell population heterogeneity related to a development and/or a disease;

(C2) drawing a cell atlas;

(C3) analyzing tumor cells with different clinical features; and (C4) studying an evolution and/or metastasis of a tumor cell clinically.

In embodiments of the present disclosure, the multi-dimensional analysis for cell epigenomics may be a multi-dimensional analysis for single-cellular epigenomics, or be a multi-dimensional analysis for multi-cellular epigenomics.

DETAILED DESCRIPTION

Figure 1:
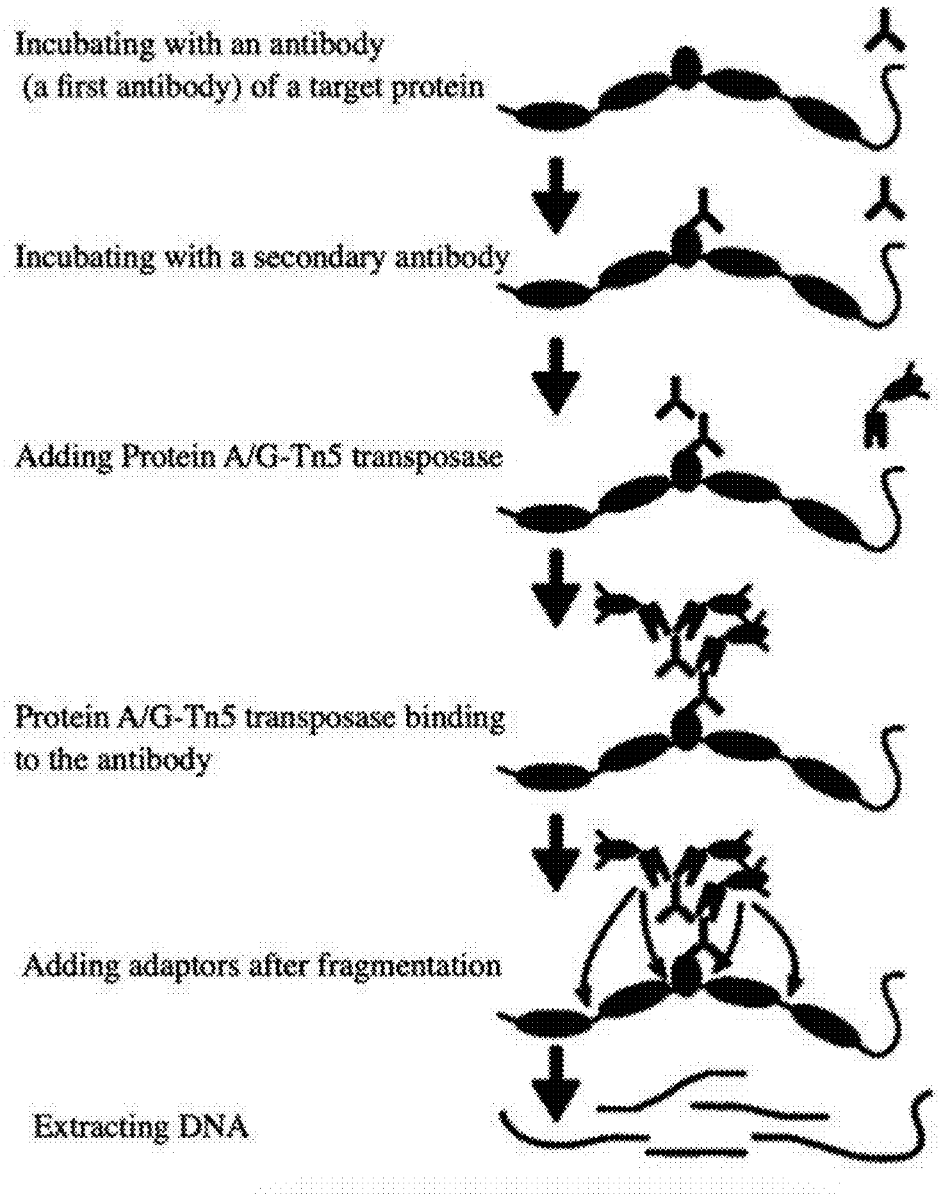
FIG. 1 is a schematic diagram of a CUT&Tag method.
Figure 2:
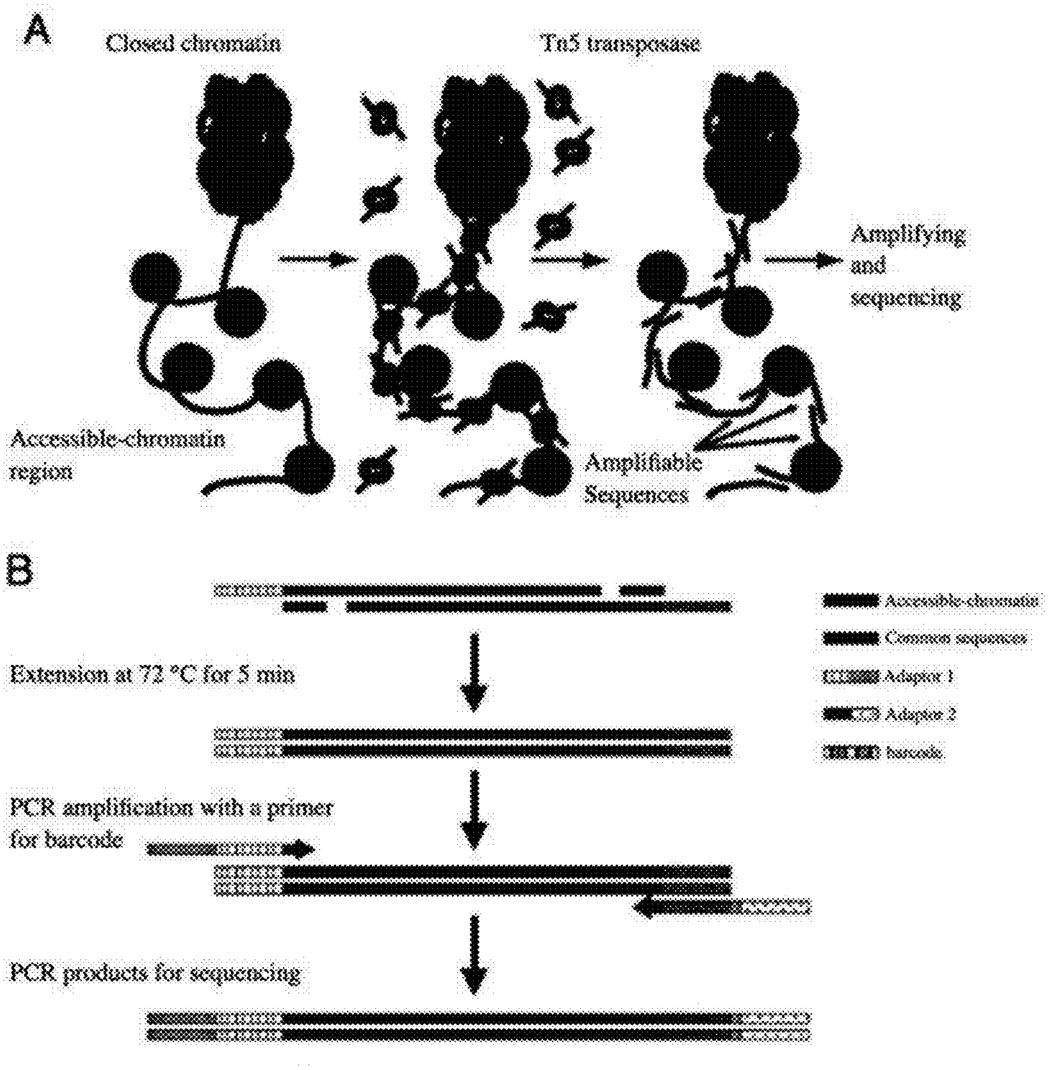
FIG. 2 is a schematic diagram of an ATAC-seq method, in which A is a schematic diagram of breaking genome sequence by a Tn5 transposase binding to an accessible-chromatin region; and B is a schematic diagram of an ATAC-seq library preparation.

Embodiments provided below are used to understand the present disclosure, thus shall not be construed to limit the present disclosure. The experimental methods in the following embodiments are conventional methods unless otherwise stated. The experimental materials used in the following embodiments are purchased from conventional biochemical reagent stores, unless otherwise stated. The quantitative experiments in the following embodiments are set for at least three duplications, and the average is taken as the result.

Example 1: Multi-Dimensional Analysis of Cellular Epigenomics

I. Multi-Dimensional Analysis of Single Cellular Epigenomics

Test cells were K562 cells.

1. Cell Pretreatment (0.5-1 h)

Note: All steps before cell infiltration were performed at room temperature to minimize the pressure on cells. It is recommended to avoid cavitation and severe vortex vibration during resuspension.

1.1 Fresh cells (500,000 to 1,000,000 cells) were collected and counted at room temperature, which were centrifuged at a low speed, i.e., 600×g for 3 min at room temperature (23-28 °C, the same below) to discard the liquid.

1.2 At least one time volume of a Wash Buffer was added to resuspend the cells, and centrifuged at the low speed (i.e., 600×g for 3 min) at room temperature to discard the liquid.

The Wash Buffer was prepared with 20 mM HEPES in pH 7.5; 150 mM NaCl; 0.5 mM Spermidine; and 1× Protease inhibitor cocktail (Sigma-Aldrich, Cat. No. 11873580001).

Note: The cells were centrifuged at 600 g for 3 min in initial washing and incubation steps, and were centrifuged at 300 g for 3 min after a combination with pA-Tn5.

2. Change of Cell Permeability

A cell nucleus was separated by changing the cell permeability with a NP4O-Digitonin Wash Buffer, and the cells were resuspended in 1 ml of the NP4O-Digitonin Wash Buffer.

The NP4O-Digitonin Water Buffer was prepared by additionally adding 0.01% (volume percentage) NP40 and 0.01% digoxin to the water buffer, where the digoxin is BN2006 #Digitonin (5%)/brand&Invitrogen/specification&1, and its weight % is 5. The concentration of digoxin in the NP40-digoxin wash buffer is equal to the concentration of digoxin in this product after 500 times volume dilution. The 0.01% digoxin provided below has the same meaning with here.

The cell resuspension was centrifuged at 600 g for 3 min, and the supernatant was discarded, and 49 μL of the NP4O-Digitonin Wash Buffer with 2 mM EDTA were added for resuspension.

3. Binding to a First Antibody (CUT&Tag)

3.1 1 μL of the first antibody (i.e., a H3K27me3 antibody, Cell Signaling Technology, 9733, Lot 14) was added to the above sample at a volume ratio of 1:50, followed by a gentle oscillation by vortex, where 1:50-1:100 volume ratio or immune concentration recommended in the manual was used by default.

3.2 All sample tubes were placed in a shaker at room temperature for 2 h for incubation (or for incubating at 4 °C. overnight). During shaking, the liquid should be kept at the bottom and side of the tubes.

4. Binding to a Secondary Antibody 4.1 All sample tubes were removed from the shaker, and 1 ml of the NP4O-Digitonin Wash buffer was added for washing once, and then centrifuged at 600 g for 3 min to remove the supernatant, and 98 μl of the NP4O-Digitonin Wash buffer were added to resuspend the cells.

4.3 2 μL of the secondary antibody, i.e., Guinea Pig anti-Rabbit IgG (Heavy&Light Chain) antibody, Antibodies-Online ABIN101961, were added to each of the samples in 98 μl of the NP4O-Digitonin Wash buffer at a volume ratio of 1:50, followed by a gentle oscillation by vortex to mix the liquid well.

4.4 All sample tubes were placed in the shaker and incubated at room temperature for 30 min.

4.5 All sample tubes were removed from the shaker, centrifuged at 600 g for 3 min to obtain a precipitate, and the supernatant was discarded.

4.6 1 mL of the NP4O-Digitonin Wash buffer was added to each of the sample tubes, and inverted up and down for 10 times or gently oscillated by vortex to mix the liquid well, to remove the unbound antibody.

4.7 The steps 4.5 and 4.6 were repeated twice.

5. Combination with ChiTag Transposase 5.1 All sample tubes were centrifuged at 600 g for 3 min to obtain a precipitate, and the supernatant was discarded.

5.2 100 μL of a NP4O-Dig-med-buffer were added to resuspend the cells, and the cells were counted. According to the counting results, 50,000 cells were added to the NP4O-Dig-med-buffer to be resuspended to 99 μl, followed by adding 1 μl of a pA-Tn5 adapter complex.

The pA-Tn5 adapter complex was prepared by evenly mixing the ChiTag transposase and a ChIP double strand adapter mixture with a molar ratio of 1:1, and then incubating them at 25 °C for 1 h. An example of a reaction system is shown in Table 1.

TABLE 1

| Example of the reaction system for the pA-Tn5 adapter complex | |
|---|---|
| ChIP double strand adapter mixture (50 pmol/μl) | 1 μl |
| ChiTagTM (6.5 pmol/μl) | 7.7 μl |

Note:
The manufacturer's article number of the ChiTag transposase is Novoprotein M058-YH01.

The ChIP double strand adapter mixture was prepared as the following steps a-d.

a. An Annealing Buffer with a formula of: 100 μl of Tris-HCl with a concentration of 1 M, pH 7.8; 20 μl of EDTA with a concentration of 0.5 M, pH 8.0; 100 μl of NaCl with a concentration of 5 M; and 9.78 ml of NF—$H_2O$, was used to dissolve a PrimerA, a ChIP-Tn5-PrimerB and a ChIP-Tn5-PrimerC to 100 μM.

```
The PrimerA:
                                    (SEQ ID No. 1)
5'-Pho-CTGTCTCTTATACACATCT-3'.
```

The ChIP-Tn5-PrimerB: (4 primers below were mixed with equal volumes after being diluted to 10011M individually),

```
                                    (SEQ ID No. 2)
5'-TCGTCGGCAGCGTCAGGCGAAGGCGATCGAGGACGGCAGATGTGTA
TAAGAGACAG-3';

                                    (SEQ ID No. 3)
5'-TCGTCGGCAGCGTCTAATCTTAGCGATCGAGGACGGCAGATGTGTA
TAAGAGACAG-3';

                                    (SEQ ID No. 4)
5'-TCGTCGGCAGCGTCCAGGACGTGCGATCGAGGACGGCAGATGTGTA
TAAGAGACAG-3';

                                    (SEQ ID No. 5)
5'-TCGTCGGCAGCGTCGTACTGACGCGATCGAGGACGGCAGATGTGTA
TAAGAGACAG-3'.
```

The ChIP-Tn5-PrimerC: (4 primers below were mixed with equal volumes after being diluted to 10011M individually),

```
                                    (SEQ ID No. 6)
5'-GTCTCGTGGGCTCGGAATCTATCAACACCGTCTCCGCCTCAGATGT
GTATAAGAGACAG-3';

                                    (SEQ ID No. 7)
5'-GTCTCGTGGGCTCGGACCAGGAAGGCACCGTCTCCGCCTCAGATGT
GTATAAGAGACAG-3';

                                    (SEQ ID No. 8)
5'-GTCTCGTGGGCTCGGGAGAGATATTCACCGTCTCCGCCTCAGATGT
GTATAAGAGACAG-3';

                                    (SEQ ID No. 9)
5-GTCTCGTGGGCTCGGGGGAAACATGCACCGTCTCCGCCTCAGATGTG
TATAAGAGACAG-3'.
```

b. The following reaction systems were prepared respectively.

Reaction system I was prepared with 10 μl of the Primer A (100 μM); and 10 μl of the ChIP-Tn5-PrimerB (10011M).

Reaction system II was prepared with 10 μl of the Primer A (100 μM); and 10 μl of the ChIP-Tn5-PrimerC (10011M).

c. The reaction system I and the reaction system II were individually fully mixed by vortex oscillation and briefly centrifuged to make the liquid return to the bottom of the tube. The tubes were placed in a PCR amplifier to perform the following reaction procedure: 75 °C for 15 min; ° C. for 10 min; 50 °C for 10 min; 40 °C for 10 min; and 25 °C for 30 min, where a lid temperature was 105 °C.

d. The reaction system I and the reaction system II were mixed evenly in an equimolar manner after the reaction procedure, so as to obtain the ChIP double strand adapter mixture, which was stored at −20 °C.

5.3 All sample tubes were placed in a shaker and incubated at room temperature for 1 h.

5.4 All sample tubes were removed from the shaker, centrifuged at 300 g for 3 min to obtain a precipitate, and the supernatant was discarded.

5.5 1 mL of the NP4O-Dig-med-buffer was added to each of the sample tubes, and inverted up and down for 10 times or gently oscillated by vortex to mix the liquid well.

5.6 The steps 5.4 and 5.5 were repeated twice, and then the sample tubes were centrifuged at 300 g for 3 min, and the supernatant was discarded to remove the remaining unbound pA-Tn5 adapter complex.

The NP40 Dig-med-buffer is prepared with 0.01% (volume percentage) NP40; 0.01% digoxin; 20 mM HEPES, pH 7.5; 300 mM NaCl; 0.5 mM Spermidine; 1× Protease inhibitor cocktail (Sigma-Aldrich, Cat. No. 11873580001).

6. Fragmentation (1 h)

6.1 300 μL of a Tagmentation Buffer were added to each of the sample tubes, with a gentle oscillation by vortex while adding.

6.2 The sample tubes were incubated with 200 rpm at 37 °C for 60 min, and then centrifuged at 300 g for 3 min, and the supernatant was discarded.

6.3 25 μL of an ATAC transposable reagent mixture containing 5 μl of 5× TAG Buffer (BGE005B01), 16 μl of 1% BSA/PBS (A0332), 4 μl of the Tn5 adapter complex, were added to each of the sample tubes and reacted with 500 rpm at 37 °C for 30 min.

The Tn5 transposase and a Tn5 double strand adapter mixture were evenly mixed with a molar ratio of 1:1, and then incubated at 25 °C for 1 h to obtain the Tn5 adapter complex. An example of a reaction system is shown in Table 2.

TABLE 2

| Example of the reaction system for the Tn5 adapter complex | |
|---|---|
| Tn5 double strand adapter mixture (50 pmol/μl) | 1 μl |
| Tn5 transposase (0.875 U/μl, Produced by BGI, article No. BGE005) | 7.7 μl |

The Tn5 double strand adapter mixture was prepared according to the following steps a-d.

a. The Annealing Buffer with a formula of: 100 μl of Tris-HCl with a concentration of 1 M, pH 7.8; 20 μl of EDTA with a concentration of 0.5 M, pH 8.0; 100 μl of NaCl with a concentration of 5 M; and 9.78 ml of NF—$H_2O$, was used to dissolve the PrimerA, an ATAC-Tn5-PrimerB, and an ATAC-Tn5-PrimerC to 100 μM.

```
The PrimerA:
                                        (SEQ ID No. 1)
5'-Pho-CTGTCTCTTATACACATCT-3'.
```

The ATAC-Tn5-PrimerB: (4 primers below were mixed with equal volumes after being diluted to 10011M individually),

```
                                        (SEQ ID No. 10)
5'-TCGTCGGCAGCGTCTATAGCCTGCGATCGAGGACGGCAGATGTGTA
TAAGAGACAG-3';

                                        (SEQ ID No. 11)
5'-TCGTCGGCAGCGTCATAGAGGCGCGATCGAGGACGGCAGATGTGTA
TAAGAGACAG-3';

                                        (SEQ ID No. 12)
5'-TCGTCGGCAGCGTCCCTATCCTGCGATCGAGGACGGCAGATGTGTA
TAAGAGACAG-3';

                                        (SEQ ID No. 13)
5'-TCGTCGGCAGCGTCGGCTCTGAGCGATCGAGGACGGCAGATGTGTA
TAAGAGACAG-3'.
```

The ATAC-Tn5-Primer C: (4 primers below were mixed with equal volumes after being diluted to 10011M individually),

```
                                        (SEQ ID No. 14)
5'-GTCTCGTGGGCTCGGATTTATGACACACCGTCTCCGCCTCAGATGT
GTATAAGAGACAG-3';

                                        (SEQ ID No. 15)
5'-GTCTCGTGGGCTCGGCCTTAATTAACACCGTCTCCGCCTCAGATGT
GTATAAGAGACAG-3';
```

-continued

```
                                        (SEQ ID No. 16)
5'-GTCTCGTGGGCTCGGTCAGTGAGTCCACCGTCTCCGCCTCAGATGT
GTATAAGAGACAG-3';

                                        (SEQ ID No. 17)
5'-GTCTCGTGGGCTCGGACTGCCTTATCACCGTCTCCGCCTCAGATGT
GTATAAGAGACAG-3'.
```

b. The following reaction systems were prepared respectively.

Reaction system I was prepared with 10 μl of the Primer A (100 μM); and 10 μl of the ATAC-Tn5-PrimerB (100 μM).

Reaction system II was prepared with 10 μl of the Primer A (100 μM); and 10 μl of the ATAC-Tn5-PrimerC (100 μM).

c. The reaction system I and the reaction system II were individually fully mixed with vortex oscillation and briefly centrifuged to make the liquid return to the bottom of the tube. The tubes were placed in a PCR amplifier to perform the following reaction procedure: 75 °C for 15 min; 60 °C for 10 min; 50 °C for 10 min; 40 °C for 10 min; and 25 °C for 30 min, where a lid temperature was 105 °C.

d. The reaction system I and the reaction system II were mixed evenly in an equimolar manner after the reaction procedure, so as to obtain the Tn5 double strand adapter mixture, which was stored at −20 °C.

7. Droplet Generation & PCR 7.1 Preparation of Magnetic Beads 7.1.1 Referring to an article of stLFR published by BGI on a preparation method for magnetic beads, i.e., Efficient and unique co-barcoding of second-generation sequencing reads from long DNA molecules enabling cost effective and accurate sequencing, haplotyping, and de novo assembly, //genome.cshlp.org/content/early/2019/04/02/gr.245126.118, surfaces of the magnetic beads (Spherotech, USA, article No. SVM-200-4, //www.spherotech.com/coa mag par.htm) were embedded with oligonucleotides to obtain magnetic beads with oligonucleotides on the surface, i.e., Tn-Beads.

7.1.2 300,000 Tn-Beads were put into a 0.2 ml low adsorption PCR tube, which was then statically placed in the magnetic stand for 2 min, and the supernatant was discarded.

7.1.3 The PCR tube was removed from the magnetic stand and 200 μl of 1× Water Buffer A containing 1 mM EDTA, Cat. AM9260, and 9 mg/ml 85% KOH, Cat. P5958-250G were added. The magnetic beads were mixed well by blowing with a 200 μl low adsorption pipette tip and incubated at room temperature for 5 min.

7.1.4 After incubation, the PCR tube was statically placed in a magnetic stand for 2 min, and the supernatant was discarded.

7.1.5 The PCR tube was removed from the magnetic stand and 200 μl of 1× Water Buffer A were added. The magnetic beads were mixed well by blowing with a 200 μl low adsorption pipette tip and then were statically placed in a magnetic stand for 2 min, and the supernatant was discarded.

7.1.6 The PCR tube was removed from the magnetic stand and 200 μl of a Wash Buffer B prepared by 500 μl of 1 M Tris-HCl, Cat. 15567027; 300 μl of 5 M NaCl, Cat. 55150; 50 μl of 10% Tween-20; and 9.15 ml $H_2O$ were added. The magnetic beads were mixed well by blowing with a 200 μl low adsorption pipette tip and then were statically placed in a magnetic stand for 2 min, and the supernatant was discarded. The above step was repeated once.

7.1.7 200 μL of the Wash Buffer B were added, and the supernatant was discarded after the nuclear preparation was completed, and in this step, the supernatant should be removed as much as possible.

7.1.8 The PCR tube was removed from the magnetic stand and 100 μl of a Beads Resuspension Buffer was added to suspend the magnetic beads. The tube was placed on ice, waiting for loading to a sequencer.

7.1.9 The Beads Resuspension Buffer was prepared according to Table 2 below.

TABLE 2

Beads Resuspension Buffer Preparation System

| Composition | Volume (μl) |
|---|---|
| 0.1% SDS | 40 |
| ATAC Bead Buffer | 58 |
| Tn Primer (20 μM) | 1 |
| 183 + C Primer (20 μM) | 1 |
| Total volume | 100 |

The ATAC Bead Buffer was prepared with 20 μl of 5× Fidelity Buffer (KK2102), 3 μl of 10 mM dNTP Mix (18427013), 7 μl of 25 mM $MgCl_2$ (20303), 16.7 μl of 60% Optiprep Density Gradient Medium (D1556-250ML), and 11.3 μl of NF—$H_2O$.

```
The Tn Primer:
                                    (SEQ ID No. 18)
5'-CGTAGCCATGTCGTTCTG-3'.

The 183 + C Primer:
                                    (SEQ ID No. 19)
5'-GAGACGTTCTCGACTCAGCAGAGTCTCGTGGGCTCGG-3'.
```

7.2 Preparation of cell nuclei 7.2.1 The cell nuclei after the transposition in the step 6.3 were taken to be counted. According to the concentration of the nucleus, 10,000 nuclei were added to a Nuclei Resuspension Buffer.

7.2.2 The Nuclei Resuspension Buffer was prepared according to Table 3 below.

TABLE 3

Nuclei Resuspension Buffer Preparation System

| Composition | Volume (μl) |
|---|---|
| Nuclei | n |
| KAPA Hifi DNA polymerase (KK2102) | 8 |
| ATAC Nuclei Buffer | 46.7 |
| NF-$H_2O$ | 45.3-n |
| Total volume | 100 |

The ATAC Nuclei Buffer was prepared with 20 μl of 5× Fidelity Buffer (KK2102), 3 μl of 10 mM dNTP Mix (18427013), 7 μl of 25 mM $MgCl_2$ (20303), and 16.7 μl of 60% Optiprep Density Gradient Medium (D1556-250ML).

7.3 Droplet generation with BGI DNBelab C4 portable single cell system 7.3.1 A protective film on a surface of a chip (Dow Corning 184) was removed, and the chip was place in a chip slot area of the droplet generator.

7.3.2 100 μL of Bio-rad Oil (1864006) were added to a collection tube, whose cap was tightened, and the collection tube was placed vertically on a fixed frame.

7.3.3 An A end of a connecting tube, which is through the cap and contacts the bottom of the collecting tube, was put into an Outlet hole of the chip.

7.3.4 An initial position of a 50 ml syringe piston was adjusted to 28 ml, and the syringe was placed on the fixed frame. A needle was used to connect the syringe and a B end of a connecting tube, which is through the cap but does not contact the bottom of the collecting tube.

7.3.5 The cells were gently mixed with a pipette, and 100 μl of cell resuspension were added to a Cells hole of the chip, ensuring no bubbles at the bottom of the cells hole.

7.3.6 The magnetic beads were gently mixed by blowing, and 100 μl of the magnetic beads were added to a Beads hole of the chip, ensuring no bubbles at the bottom of the beads hole.

7.3.7 The Bio-rad Oil was quickly added to the Oil hole of the chip, in which 400 μl of the Oil were added first, and additional Oil was needed to be added during the experiment.

7.3.8 The piston of the syringe was quickly pulled to a scale of 30 ml, and the syringe was fixed on the fixed frame.

7.3.9 A timer was started to count the time when collecting liquid droplets and if at a test stage, the liquid may be waited for running out, and it should be noted to replenish the oil.

7.3.10 After the generation of droplets, the collection cap of the collection tube was immediately unscrewed, and the connecting tube in the Outlet holes of the chip was pulled out and vertically stretched to make the droplets in the connecting tube flow into the collection tube, and then replaced by an ordinary collection tube cap.

7.3.11 The liquid droplets were transferred into an eight-tube strip, where it should be noted that a liquid level of the droplets shall not exceed 100 μl. Then 100 μl of mineral oil were added to cover a surface of the droplets. With covered by an eight-tube strip cap, the droplets were performed for a PCR amplification according to the following Table 4.

TABLE 4

PCR procedure for the amplification within the droplets

| cycle | denaturing | annealing | extending | terminating |
|---|---|---|---|---|
| 1 | | | 72 °C, 30 min | |
| 1 | 98 °C, 30 s | | | |
| 10 | 98 °C, 10 s | | | |
| | | 63 °C, 30 s | | |
| | | | 72 °C, 1 min | |
| 1 | | | 72 °C, 5 min | |
| 1 | | | | 12 °C, hold |

There is a breakpoint, and after the PCR, the droplets may be placed at 4 °C for 72 h.

8. Demulsification & Amplification Outside the Droplets 8.1 Demulsification 8.1.1 After the PCR, the droplets was transferred to a new 1.5 ml low adsorption centrifuge tube, and 100 μl of Additive B (Perfluoro-1-octnaol, A63881) was added, mixed upside down, and centrifuged at 1000 g for 1 min, and then statically placed in the magnetic stand for 1 min, and the liquid was removed.

8.1.2 500 μL of Wash Buffer F with a formula of 10 ml of TE Buffer, 10 μl of 10% Tween-20, AM9820 were added and mixed upside down, and the tube was centrifuged at 1,000 g for 1 min, and then was statically placed in the magnetic stand for 1 min, and the supernatant was discarded.

8.1.3 The above step was repeated once. After that, the following enzyme treatment system was added after discarding the supernatant.

8.2 Enzyme Treatment 8.2.1 The enzyme treatment system was prepared in advance according to the following Table 5.

TABLE 5

| Enzyme treatment system | |
|---|---|
| Composition | Volume (μl) |
| NF-$H_2O$ | 170 |
| ATAC Enzyme II | 10 |
| ATAC Reaction Buffer | 20 |
| Total volume | 200 |

The ATAC Enzyme II is an EXO I (M0293S).

The ATAC Reaction Buffer is 10×EXO I Buffer (B0293s).

8.2.1 200 μL of the treatment system were added to the PCR tube with the magnetic beads (without blowing).

8.2.3 The tube was incubated in a metal bath at 37 °C with 1000 rpm for 45 min.

8.2.4 After the incubation, the tube was centrifuged briefly and 1 ml of Water Buffer E with a formula of 9.75 ml of TE Buffer, 0.25 ml of 20% SDS, AM9820, was added and mixed upside down to stop the reaction.

8.2.5 After centrifugation at 1,000 g for 1 min, the tube was statically placed in the magnetic stand for 1 min, and the supernatant was discarded.

8.2.6 500 μL of Wash Buffer F with a formula of 10 ml of TE Buffer, 10111 of 10% Tween-20, AM9820, were added once again, and mixed them upside down. The tube was centrifuged at 1,000 g for 1 min, and then placed in the magnetic stand for 1 min, and the supernatant was discarded. This step was repeated twice.

8.2.7 Maintaining an adsorption for the magnetic beads, 400 μl of PCR Ready Mix were added and mixed with the magnetic beads well by blowing, and then the mixed magnetic beads were evenly divided into an eight-tube strip. 400 μL of the PCR Ready Mix were added again to wash the tube, and then evenly divided into the eight-tube strip. Note: This step should be operated at 4 °C to avoid inactivation of the PCR Ready Mix.

8.3 PCR Amplification 8.3.1 A PCR Ready Mix was prepared according to the following Table 6.

TABLE 6

| PCR Ready Mix preparation system | |
|---|---|
| Composition | Volume (μl) |
| ATAC Enzyme III (2× KAPA HiFi HotStart Ready Mix, KK2602) | 50 |
| Tn Primer (20 μM) | 2 |
| 183-pho Primer (20 μM) | 2 |
| 60% Optiprep Density Gradient Medium | 16.7 |
| NF-$H_2O$ | 29.3 |
| Total volume | 100 |

```
The Tn Primer:
                                    (SEQ ID No. 18)
5'-CGTAGCCATGTCGTTCTG-3';

The 183-pho Primer:
                                    (SEQ ID No. 20)
5'-pho GAGACGTTCTCGACTCAGCAGA-3'.
```

8.3.2 The PCR Ready Mix was divided according to the step 8.2.7, and the reaction mixture was mixed by vortex and centrifuged briefly.

8.3.3 A reaction in a PCR amplifier was according to the conditions in Table 7 below, and the lid temperature was set at 105 °C.

TABLE 7

| PCR Procedure | | | | |
|---|---|---|---|---|
| cycle | denaturing | annealing | extending | terminating |
| 1 | 98 °C, 30 s | | | |
| 15 | 98 °C, 10 s | | | |
| | | 63 °C, 30 s | | |
| | | | 72 °C, 1 min | |
| 1 | | | 72 °C, 5 min | |
| 1 | | | | 12° C., hold |

Note:
For different samples, a number of PCR cycles may be adjusted accordingly.

There is a breakpoint, and the PCR product may be stored at 4 °C for 24 h. After the PCR, a quantitation with Qubit was used to determine whether there is a problem in the preliminary treatment. If the concentration of product is less than 2 ng/μl, it indicates that the sample treatment is failed, and there is no need to continue the subsequent operations.

9. Purification with 1.2× magnetic beads 9.1 AgencourtAMPure XP was taken out in advance and placed at room temperature for at least 30 min for a balance, and was mixed well by shaking before use.

Note: There is a liquid evaporation during the PCR reaction. If the liquid evaporation is significant, it is necessary to re-quantitate the liquid volume V and supplement it to 800 μl with $H_2O$.

9.2 The PCR product was transferred into a new 2 ml centrifuge tube, and 960 μl of the AgencourtAMPure XP were put into the tube by pipette, vortexed them until completely mixed, and incubated at room temperature for 8 min.

9.3 The tube was placed in the magnetic stand for 5 min, in which the magnetic beads were absorbed, and the liquid was become clear.

9.4 The supernatant was discarded, without touching the magnetic beads.

9.5 200 μL of 80% ethanol were added for standing for 30 s, and the supernatant was discarded. This step was repeated twice.

9.6 The sample was placed in the magnetic stand for drying until the surface of the magnetic beads was not reflective (about 2-5 min).

9.7 The PCR tube was removed from the magnetic stand and 50-100 μl of NF—$H_2O$ were added to dissolve the sample, which were blown for 10 times until mixed well, and placed at room temperature for 5 min.

9.8 The PCR tube was statically placed in the magnetic stand for 3 min, and the liquid was clear.

9.9 The liquid was taken out without touching magnetic beads.

9.10 1 μL of the liquid was taken to determine a concentration with Qubit, and the product was diluted to about 2 ng/μl according to the concentration, and then 1 μl of the product was taken for 2100HS testing, and the length of library fragments was 200 bp-600 bp.

10. Single-strand thermal denaturation (with 200-400 ng DNA input per reaction)

The reaction system is shown in Table 8, and the parameter settings are shown in Table 9.

TABLE 8

| Reaction system of the single-strand thermal denaturation | |
|---|---|
| Composition | Volume |
| DNA mix | X µl |
| 153 + 181 Splint oligo (20 µM) | 3 µl |
| NF-$H_2O$ | Make up to 50 µl |
| Total volume | 50 µl |

The DNA mix was the mixed DNA sample obtained from the above purification step.

```
The 153 + 181 Splint oligo:
                                  (SEQ ID No. 21)
5'-CGAGAACGTCTCCGTAGCCATGTC-3'.
```

TABLE 9

| The parameter settings for the single-strand thermal denaturation | | |
|---|---|---|
| cycle | temperature | time |
| 1 | 95 °C | 3 min |
| 1 | 4 °C | Forever |

10. Cyclization

A reaction system of the cyclization is shown in Table 10.

TABLE 10

| Reaction system of the cyclization | |
|---|---|
| Composition | volume |
| DNA mix obtained from the former step | 50 µl |
| 10× TA buffer | 6 µl |
| 100 mM ATP | 0.6 µl |
| T4 DNA Ligase (400 U/µl) | 0.6 µl |
| TE Buffer | 2.8 µl |
| Total volume | 120 µl |

The manufacturer's article number of 10×TA buffer is EPICENTRE TA6160.

The above reaction system was prepared and oscillated by vortex, and then centrifuged for 5 s, incubated at 37 °C for 45 min and held at 4 °C.

11. Enzyme digestion

An enzyme digestion system is shown in Table 11.

TABLE 11

| Enzyme digestion system | |
|---|---|
| Composition | volume |
| Cyclized product mix obtained from the former step | 60 µl |
| 10× TA buffer | 0.4 µl |
| EXO I (20 U/µl) | 1.95 µl |
| EXO III (100 U/µl) | 0.65 µl |
| TE Buffer | 1 µl |
| Total volume | 64 µl |

The manufacturer's article number of 10×TA buffer is EPICENTRE TA6160.

The above reaction system was prepared and oscillated by vortex, and then centrifuged for 5 s, incubated at 37 °C for 30 min and held at 4 °C. After that, 4 µl of 0.1 mM EDTA (AMBION, AM9260G) were added to stop the reaction.

12. Magnetic Beads Purification 12.1 90 µL of PEG32 beads were added to the above reaction solution, and stirred by vortex to mix them well, and incubated at room temperature for 10 minutes.

12.2 The reaction tube was briefly centrifuged and placed in the magnetic stand to separate the magnetic beads and liquid. After the liquid was clarified (for about 5 minutes), the liquid was removed carefully.

12.3 The EP tube was kept in the magnetic stand all the time and 200 µl of freshly prepared 80% ethanol were added to wash the magnetic beads. The supernatant was carefully removed after incubation at room temperature for 30 seconds.

12.4 The above step was repeated and the washing was performed twice in total.

12.5 The EP tube was kept in the magnetic stand all the time and a cover of the tube was opened to dry the magnetic beads with air for 3 minutes.

12.6 The EP tube was removed from the magnetic stand and added with 32 µl of sterilized ultrapure water for elution. The magnetic beads were oscillated by vortex or gently blown with a pipette to mix well. The tube was briefly centrifuged and placed in a magnetic stand to separate the magnetic beads and liquid. After the liquid was clarified (for about 2 minutes), the liquid was carefully removed into a sterilized EP tube and was stored at −20 °C, which obtained here was the final library.

12.7 1 µL of purified product was taken to determine the concentration of ssDNA.

The result was 2.89 ng/µl (*Empirical values for a concentration of ssDNA should be ng/µl, and for a total amount should be 80-100 ng).

13. High-throughput sequencing

The BGI-SEQ500 was used to sequence the final library with pair-ended sequencing, and the sequencing method was PE50+26+10.

14. Data Analysis

II. Multi-dimensional analysis of multicellular epigenomics 1-6. Steps 1-6 were the same as the steps 1-6 of the method for multi-dimensional analysis of single-cellular epigenomics.

7. Purification with a column was performed by using QIAamp DNA Mini Kit (Article No. 51304), which contains PB Buffer, PE Buffer and centrifuge column as described below.

7.1 125 µL (5 times volume) of the PB Buffer were added to the sample after the reaction in step 6.3, and the mixture was mixed well by blowing.

7.2 A filter column was placed in a 2 ml centrifuge tube and the mixture of the step 7.1 was added to the filter column.

7.3 The column together with the centrifuge tube was placed into a centrifuge and centrifuged at 13,000 rpm for 1 minute until all samples pass through the column, and the waste liquid was discarded.

7.4 750 µL of the PE Buffer were added into the column, which was then centrifuged at 13,000 rpm for 1 minute, and the waste liquid was discarded.

7.5 The column was centrifuged for 1 minute to completely remove the residual alcohol.

7.6 The column was placed in a new 1.5 ml centrifuge tube.

7.7 20 µL of TE Buffer (AM9858) were added to elute the DNA, with elution for 1 minute, the tube was centrifuged at 13,000 rpm for 1 minute to collect the liquid.

8. PCR Amplification 8.1 A PCR Ready Mix was prepared according to Table 12 below.

TABLE 12

PCR Ready Mix Preparation System

| Composition | Volumn (μl) |
|---|---|
| 2× KAPA Ready Mix | 25 |
| Bulk-N5 Primer (20 μM) | 2 |
| 183 + C-pho Primer (20 μM) | 2 |
| The DNA obtained from the step 7.7 | 19 |
| NF-$H_2O$ | 2 |
| Total volume | 50 |

```
The Bulk-N5 Primer:
                                        (SEQ ID No. 22)
5'-CGTAGCCATGTCGTTCTGCGTCGTCGGCAGCGTC-3';

The 183 + C-pho Primer:
                                        (SEQ ID No. 23)
5'-pho
GAGACGTTCTCGACTCAGCAGAGTCTCGTGGGCTCGG-3'.
```

8.2 The reaction system was mixed by vortex and centrifuged briefly.

8.3 A reaction was performed with a PCR amplifier according to the conditions in Table 13 below, and the lid temperature was set at 105 °C.

TABLE 13

PCR Procedure

| cycle | denaturing | annealing | extending | terminating |
|---|---|---|---|---|
| 1 | 72 °C, 5 min | | | |
| 1 | 98 °C, 30 s | | | |
| 15 | 98 °C, 10 s | | | |
| | | 63 °C, 30 s | | |
| | | | 72 °C, 5 s | |
| 1 | | | 72 °C, 1 min | |
| 1 | | | | 12 °C, hold |

Note:
For different samples, a number of PCR cycles may be adjusted accordingly.

There is a breakpoint, and the PCR products may be stored at 4 °C for 24 h. After the PCR, a quantitation with Qubit was used to determine whether there is a problem in the preliminary treatment, and if the concentration of the product is less than 5 ng/μl, it indicates that the sample treatment is failed, and there is no need to continue the subsequent operations.

9-14. Steps 9-14 were same as the steps 9-14 of the method for multi-dimensional analysis of single-cellular epigenomics.

Results and Analysis

Figure 3:
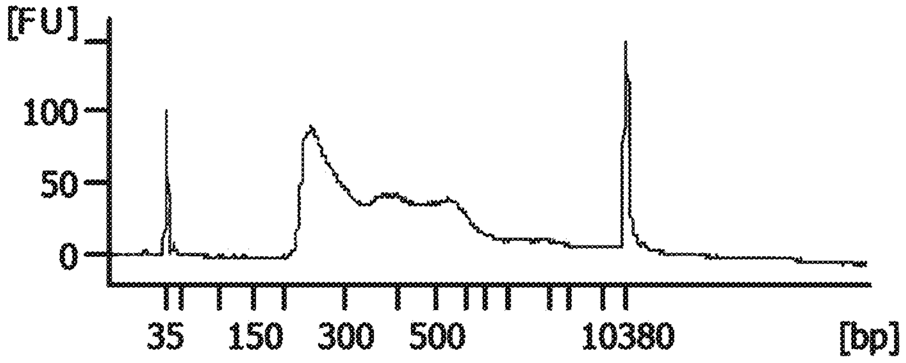
FIG. 3 is a graph showing a quality testing result of DNA products obtained from single cells.
Figure 4:
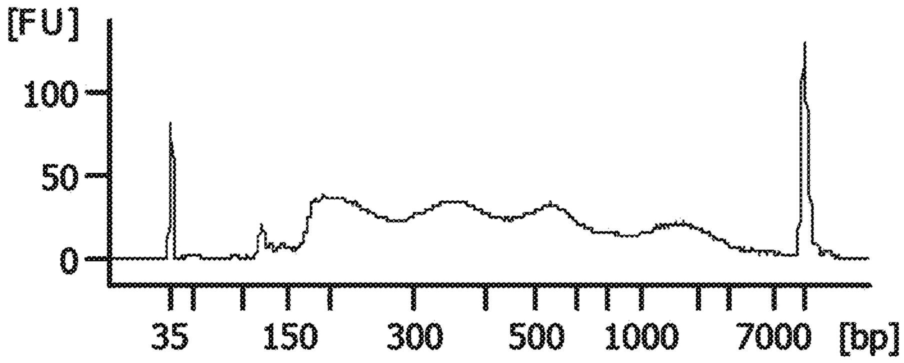
FIG. 4 is a graph of showing a quality testing result of DNA products obtained from multiple cells.

The quality testing results of the DNA products obtained from single cells are shown in FIG. 3. The quality testing results of the DNA products obtained from multiple cells are shown in FIG. 4. It can be seen from FIG. 3 and FIG. 4 that DNA fragments with 200-500 bp were enriched by both methods provided in single-cell and multi-cell Examples, indicating that the experiments is feasible.

Figure 5:
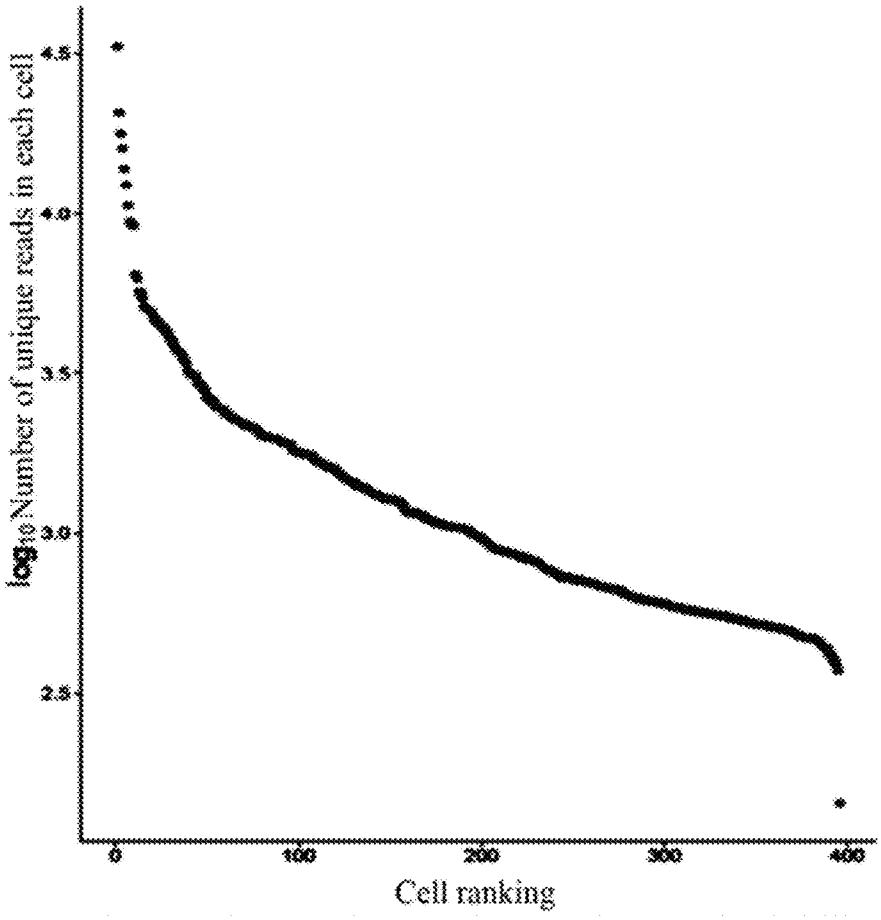
FIG. 5 shows a unique reads number obtained from single-cellular CUT&Tag data.
Figure 6:
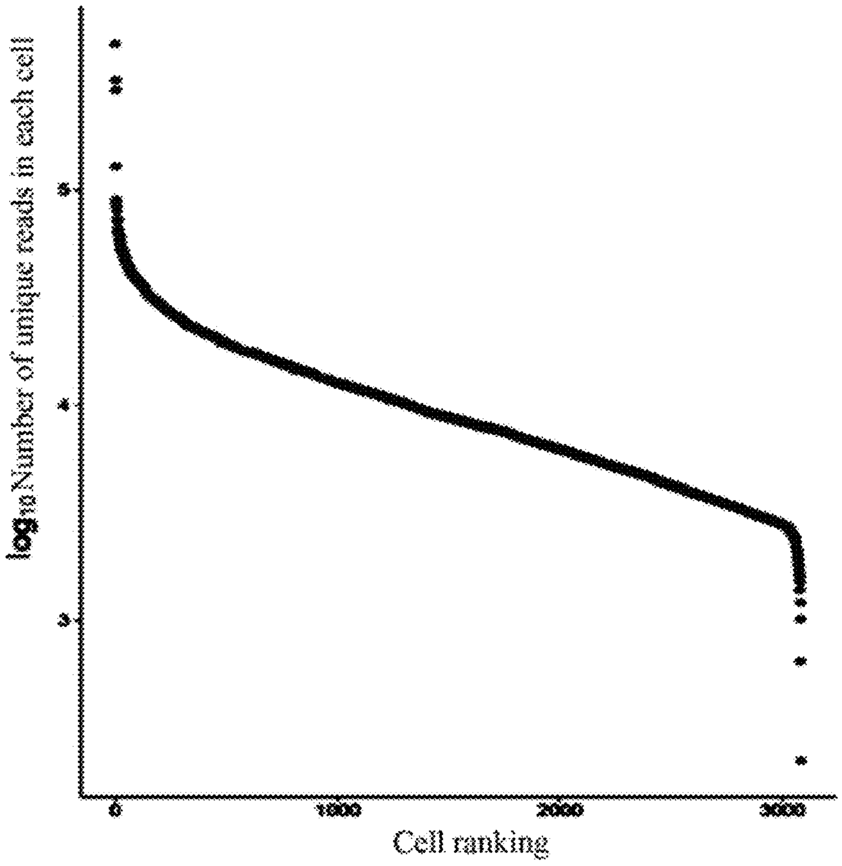
FIG. 6 shows a unique reads number obtained from single-cellular ATAC-seq data.

The results of the single-cellular analysis are shown in Table 13, FIG. 5 and FIG. 6. FIG. 5 shows a unique reads number obtained from single cellular CUT&Tag data. FIG. 6 shows a unique reads number obtained from single-cellular ATAC-seq data. It can be seen from Table 13, FIG. 5 and FIG. 6 that, the single-cell data, including a number of cells and a total number of reads obtained by Example 1 as shown in Table 13, could support the following analysis. FIGS. 5 and 6 respectively show a number of reads that could be captured by the CUT&Tag data and by the ATAC-seq data of each cell in Example 1, where in part of the CUT&Tag data, more than 100 cells and each of them could be captured for more than 1,000 reads; and in the ATAC-seq data, most cells and each of them could be captured for more than 5,000 reads. The captured available reads could support the following analysis.

TABLE 13

Single-cellular sequencing results

| | CUT&Tag | ATAC-seq |
|---|---|---|
| Cell number | 376 | 2308 |
| Total number of reads | 12308078 | 586454498 |
| Number of mapped reads | 12008982 | 571379934 |
| Ratio of mapped reads | 97.57% | 97.43% |
| Q30 | 91.5% | 93.4% |

Figure 7:
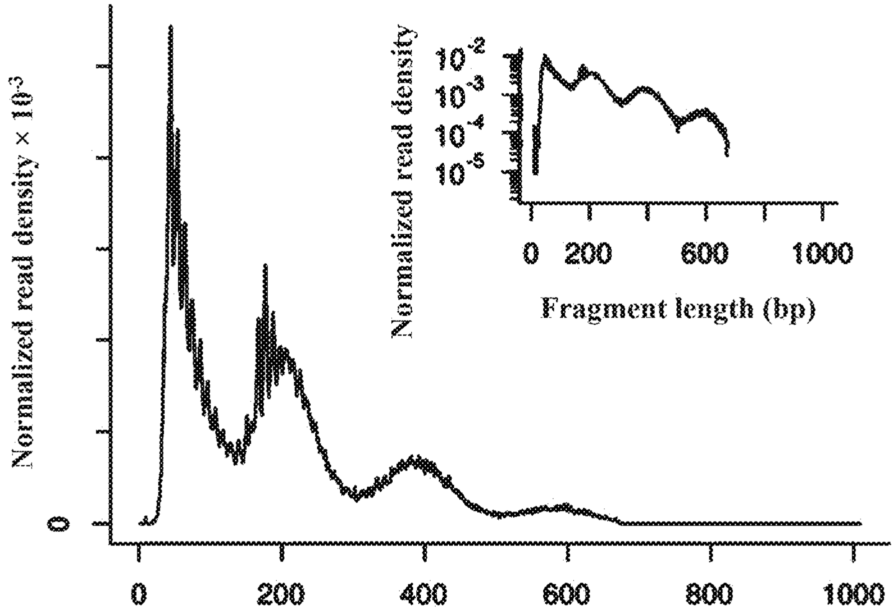
FIG. 7 is a graph showing a distribution of fragments obtained from single-cellular CUT&Tag.
Figure 8:
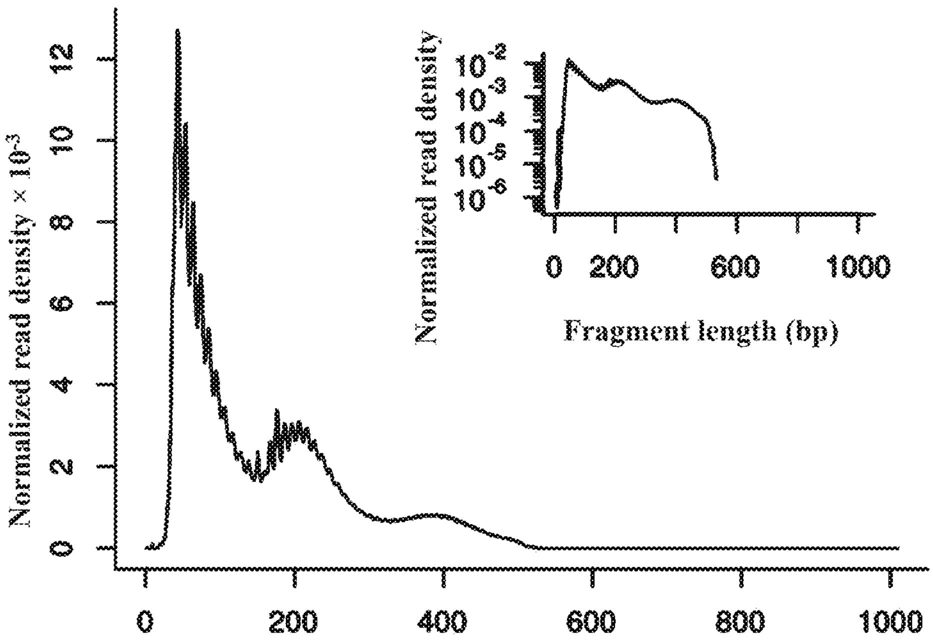
FIG. 8 is a graph showing a distribution of fragments obtained from single-cellular ATAC-seq.

FIG. 7 and FIG. 8 show distributions of fragments obtained from the single-cellular data of the CUT&Tag and ATAC-seq, respectively. FIG. 7 shows peaks of different fragment sizes obtained from the single-cellular CUT&Tag, which represents periodic changes of nucleosomes, indicating that numbers of different nucleosomes could be obtained, thereby verifying the accuracy of the experiment. FIG. 8 shows the single-cellular data of the ATAC-seq, in which the main peak is the first peak, indicating that the ATAC-seq mainly captures DNA in the accessible-chromatin region.

The results of single-cellular analysis are shown in Table 14. It can be seen from Table 14 that, the multi-cellular data, including a number of cells and a total number of reads obtained in Example 2 as shown in Table 14, could support the following analysis.

TABLE 14

Multi-cellular sequencing results

| | CUT&Tag | ATAC-seq |
|---|---|---|
| Total number of reads | 3982091 | 472527602 |
| Number of mapped reads | 8821920 | 571379934 |
| Ratio of mapped reads | 99.19% | 98.63% |

Figure 9:
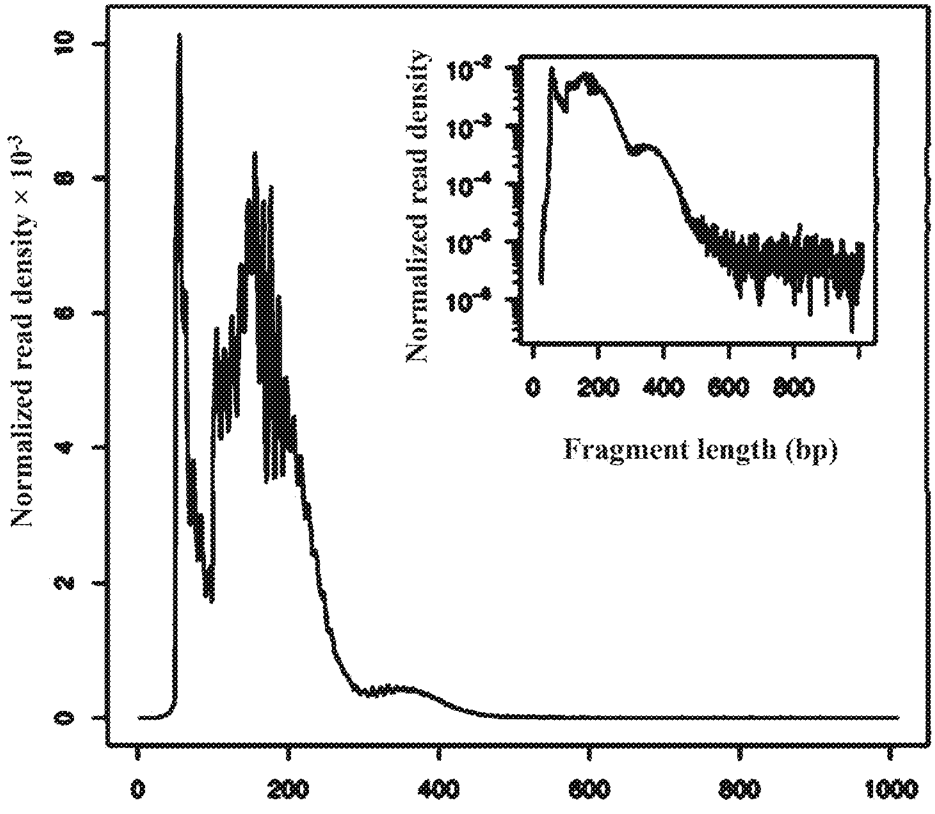
FIG. 9 is a graph showing a fragments distribution obtained from multicellular CUT&Tag.
Figure 10:
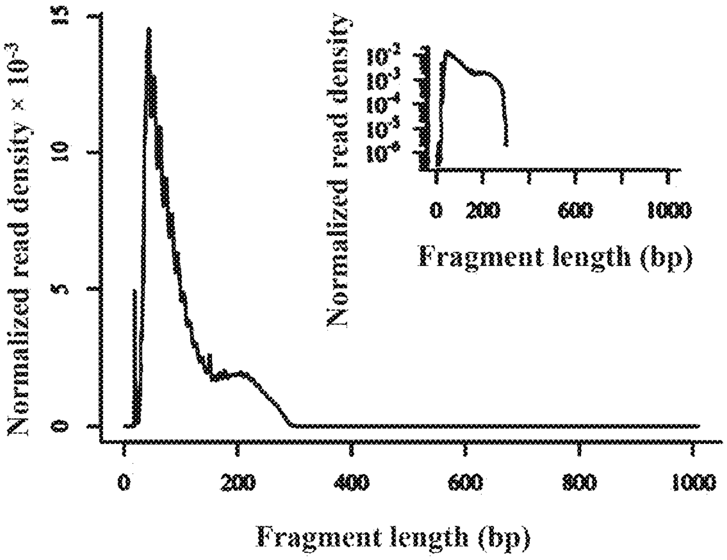
FIG. 10 is a graph showing a fragments distribution obtained from multicellular ATAC-seq.

FIG. 9 shows a fragments distribution acquired from the multi-cellular CUT&Tag, and FIG. 10 shows a fragments distribution acquired from the multi-cellular ATAC-seq. From FIG. 9 and FIG. 10, it can be seen that FIG. 9 and FIG. 10 show the distribution of fragments obtained from multi-cellular CUT&Tag data and ATAC-seq data, respectively. FIG. 9 shows peaks of different fragment sizes obtained from multi-cellular CUT&Tag, which represents periodic changes of nucleosomes, indicating that numbers of different nucleosomes could be obtained, thereby verifying the accuracy of the experiment. FIG. 10 shows the multi-cellular data of the ATAC-seq, in which the main peak is the first peak, indicating that the ATAC-seq mainly captures DNA in the accessible-chromatin region.

Figure 11:
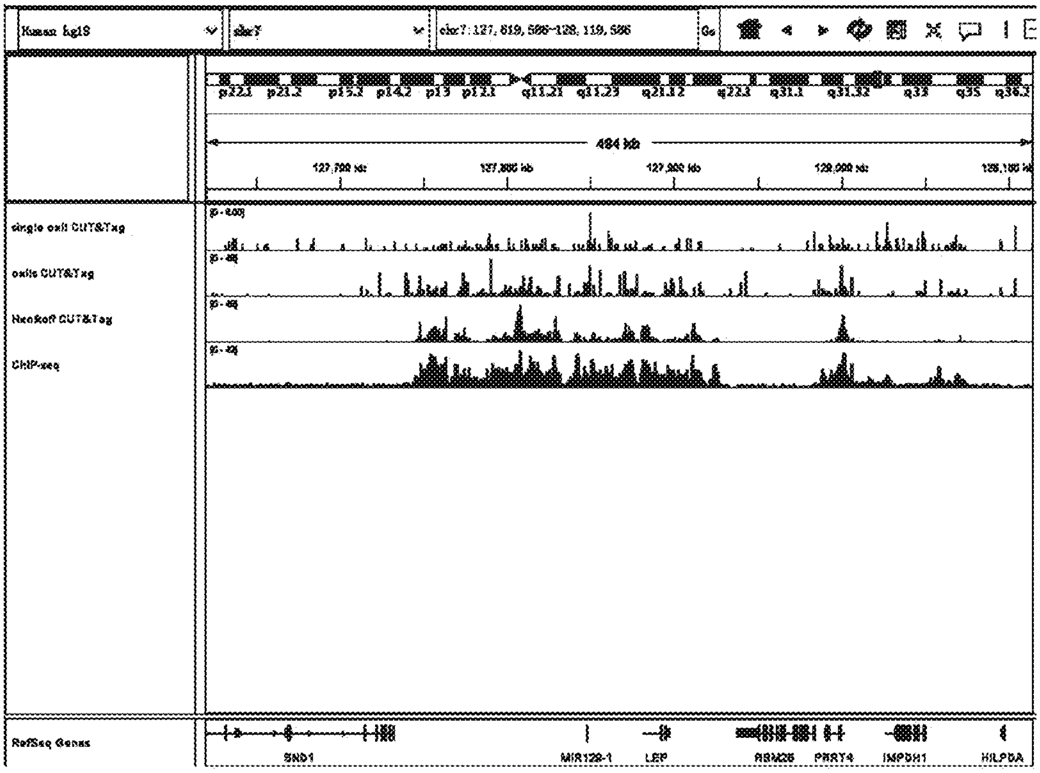
FIG. 11 shows a peak distribution of part of CUT&Tag data.

FIG. 11 shows a peak distribution of part of the CUT&Tag data, in which the first red frame (single cell CUT&Tag)

represents the data obtained in step I of Example 1 of the present disclosure; the second black frame (cells CUT&Tag) in the middle represents the data obtained in step II; the third green frame (Henikoff CUT&Tag) is CUT&Tag data obtained by a reference document (//doi.org/10.1038/s41467-019-09982-5); and the fourth blue frame (ChIP-seq) is the data in the ChIP-seq database. The peak distributions of the four pieces of data are basically consistent, proving that the CUT&Tag data obtained in step I and step II of Example 1 of the present disclosure is true and effective.

Figure 12:
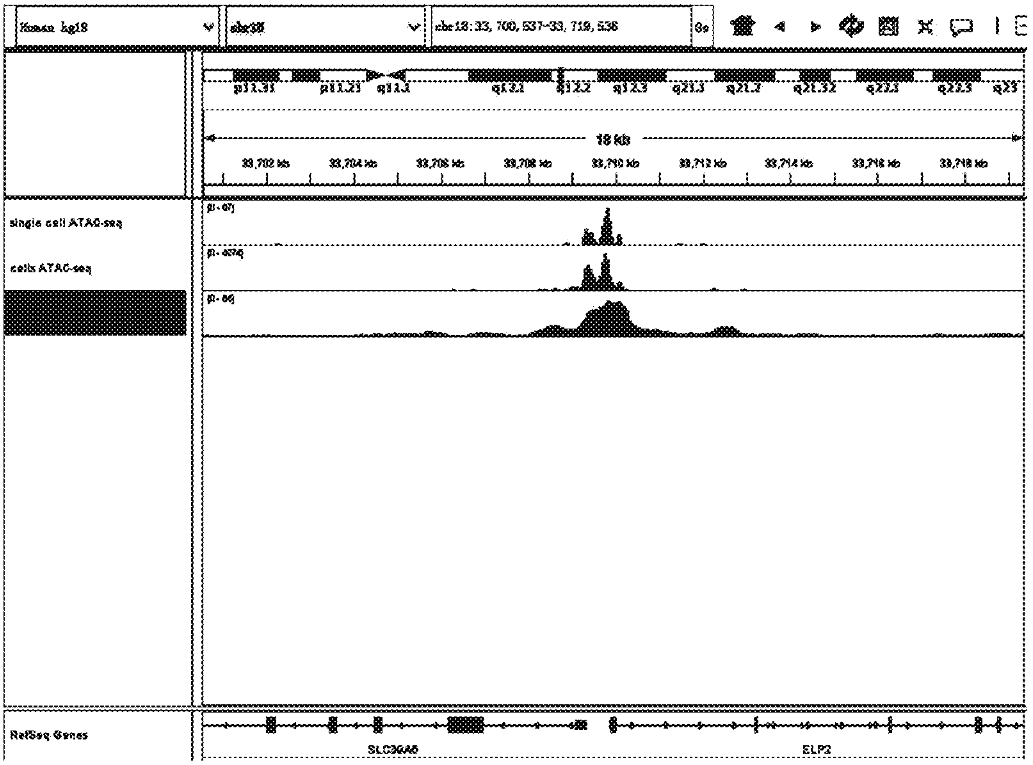
FIG. 12 shows a peak distribution of part of ATAC-seq data.

FIG. 12 shows a peak distribution of part of ATAC-seq data, in which the first red frame (single cell ATAC-seq) is the ATAC data obtained in Step I of Example 1 of the present disclosure; the second black frame (cells ATAC-seq) is the ATAC data obtained in Step II; and the third blue frame (K562 ATAC-seq) is the peak distribution of K562 cells in the ATAC-seq database. The peak distributions of the three pieces of data are basically consistent, proving that the ATAC data obtained in the Example of the present disclosure is true and effective.

Industrial Applications

The present disclosure can realize both of the ChIP-seq and ATAC-seq in cells, and the ATAC-seq provides information of an accessible-chromatin region in the cells, and ChIP-seq provides information of a sequence binding with a target protein. A combination of the two can obtain more abundant epigenetic information, which is conducive to scientific researchers for studying the heterogeneity of cell populations related to a development and a disease and drawing a cell atlas.

The method in Examples of the present disclosure combines two dimensions of epigenomics, i.e., ATAC-seq and ChIP-seq, and ultlizes a pA-Tn5 fusion protein (i.e. a ChiTag transposase) and a conventional Tn5 transposase in cells to embed different adapter sequences respectively, and analyzes the information of accessible-chromatin region and a specific protein-binding sequence at the single cell level, thus achieving a co-analysis of epigenomics in two dimensions at the single cell level, thereby obtaining more abundant epigenomics information.

The present disclosure could be used to develop a high-throughput ATAC-seq and ChIP-seq combination library kit for tumor samples and development and disease samples. In terms of scientific research applications, it can be used for researchers to study the heterogeneity of development and disease-related cell populations and to draw cell atlas, and provide more information on epigenetic regulation. It also has broad application prospects in clinical aspects. Compared with current transcriptome sequencing method based on mRNA, the method in Examples of the present disclosure is based on the chromatin genome in the nucleus, which is relatively difficult to degrade, and has a higher tolerance for a sample quality. The method in Examples of the present disclosure can analyze tumor cells with different clinical characteristics, which is of great significance for the clinical study of tumor cell evolution and metastasis. The present disclosure can capture the information of a target-protein interacted DNA sequence and the information of the accessible-chromatin region at the single-cellular level and the multiple-cellular level individually, so that the cell epigenome can be analyzed in multiple aspects, to study the epigenetic regulation mechanism of cells related to development and disease.

What is claimed is:

1. A method for multi-dimensional analysis of cell epigenomics, comprising the following steps: utilizing a ChiTag transposase and a Tn5 transposase to respectively embed different adapter sequences in a cell; and performing a co-analysis for information of an accessible-chromatin region and a target-protein binding sequence at the cellular level, wherein the method is a method A or a method B, wherein the method A is a method for multi-dimensional analysis of single-cell epigenomics, comprising the following steps:

(A1) changing the permeability of a cell to be tested;

(A2) adding an antibody corresponding to the target protein to the cell after the treatment of the step (A1) for a first incubation;

(A3) adding a secondary antibody to the cell after the treatment of the step (A2) for a second incubation;

(A4) adding the ChiTag transposase to the cell after the treatment of the step (A3) for a third incubation; and (A5) adding a reaction reagent to the cell after the treatment of the step (A4) for a fourth incubation, and adding the Tn5 transposase after the fourth incubation, the method B is a method for multi-dimensional analysis of multi-cell epigenomics, comprising the following steps:

(B1) changing the permeability of a cell to be tested;

(B2) adding an antibody corresponding to the target protein to the cell after the treatment of the step (B1) for a first incubation;

(B3) adding a secondary antibody to the cell after the treatment of the step (B2) for a second incubation;

(B4) adding the ChiTag transposase to the cell after the treatment of the step (B3) for a third incubation; and (B5) adding a reaction reagent to the cell after the treatment of the step (B4) for a fourth incubation, and adding the Tn5 transposase after the fourth incubation.

2. The method according to claim 1, wherein the method A further comprises the following steps:

(A6) generating a droplet comprising a single cell with a water-in-oil structure and performing an amplification within the droplet after the reaction of the step (A5);

(A7) performing a demulsification, amplification and purification;

(A8) performing an enzyme digestion to obtain a final library; and (A9) performing high-throughput sequencing on the final library obtained in the step (A8) to analyze the information of the accessible-chromatin region and the target-protein binding sequence at a single cellular level, and the method B further comprises the following steps:

(B6) performing an amplification and purification;

(B7) performing an enzyme digestion to obtain a final library; and (B8) performing high-throughput sequencing on the final library obtained in the step (B7) to analyze the information of the accessible-chromatin region and the target-protein binding sequence at a multi-cellular level.

3. The method according to claim 1, wherein in the steps (A1) and (B1), changing the permeability of the cell to be tested is achieved by resuspending the cell to be tested in an NP40-digoxin wash buffer, the NP40-digoxin wash buffer is obtained by adding 0.01% NP40 and 0.01% digoxin to a basic wash buffer, the basic wash buffer comprises: 20 mM HEPES in pH 7.5, 150 mM NaCl, 0.5 mM spermidine, and 1× protease inhibitor.

4. The method according to claim 3, wherein each of the steps (A1) and (B1) comprises: resuspending 500,000 to 1,000,000 cells in 1 ml of the NP40-digoxin wash buffer; centrifuging the buffer and discarding a supernatant; and resuspending the cells by adding 49 μl of the NP40-digoxin wash buffer comprising 1.5-2.5 mM EDTA, and in the steps (A2) and (B2), the antibody corresponding to the target protein is directly added to a cell resuspension at the second resuspension obtained in the steps (A1) and (B1).

5. The method according to claim 1, wherein in the steps (A2) and (B2), the antibody corresponding to the target protein is an H3K27me3 antibody.

6. The method according to claim 1, wherein each of the steps (A3) and (B3) further comprises steps of washing and centrifugation at at least one of the following: before adding the secondary antibody, or after the second incubation, wherein the washing is performed with the NP40-digoxin wash buffer, and the centrifugation is performed at 600 g for 3 min.

7. The method according to claim 1, wherein each of the steps (A4) and (B4) further comprise steps of centrifugation and cell resuspension sequentially before adding the ChiTag transposase, wherein the centrifugation is performed at 600 g for 3 min, and the cell resuspension is performed by resuspending the cell with a chitag enzyme incubation buffer, and the chitag enzyme incubation buffer comprises 0.01% (volume percentage) NP40; 0.01% digoxin, 20 mM HEPES in pH 7.5; 300 mM NaCl; 0.5 mM spermidine and 1× protease inhibitor.

8. The method according to claim 1, wherein in each of the steps (A4) and (B4), a PrimerA, a ChIP-Tn5-PrimerB and a ChIP-Tn5-PrimerC are added while adding the ChiTag transposase, the PrimerA is a single strand DNA shown in SEQ ID NO: 1 modified with a phosphate group at the 5' end, the ChIP-Tn5-PrimerB is a mixture of four single strand DNAs as shown in SEQ ID NO: 2, SEQ ID NO: 3, SEQ ID NO: 4 and SEQ ID NO: 5, and the ChIP-Tn5-PrimerC is a mixture of four single strand DNAs as shown in SEQ ID NO: 6, SEQ ID NO: 7, SEQ ID NO: 8 and SEQ ID NO: 9.

9. The method according to claim 8, wherein in the steps (A4) and (B4), the ChiTag transposase is added to a cell suspension resuspended with the chitag enzyme incubation buffer, a ratio of an addition of the ChiTag transposase is adding 99 μL of the cell suspension to 1 μL of a pA-Tn5 adapter complex, wherein the pA-Tn5 adapter complex is obtained by evenly mixing the ChiTag transposase with a ChIP double strand adapter mixture at a molar ratio of 1:1 and incubating at 25 °C for 1 h, wherein a final concentration of the ChiTag transposase in the pA-Tn5 adapter complex is 5.75 pmol/μl, and the ChIP double strand adapter mixture comprises the PrimerA, the ChIP-Tn5-PrimerB and the ChIP-Tn5-PrimerC, wherein the ChIP double strand adapter mixture is prepared according to a method comprising the following steps:

step 1, preparing the following reaction systems by:

for a reaction system I, mixing the PrimerA and the ChIP-Tn5-PrimerB in an equimolar manner, and for a reaction system II, mixing the PrimerA and the ChIP-Tn5-PrimerC in an equimolar manner;

step 2, subjecting the reaction system I and the reaction system II individually to the following reaction procedure of 75 °C for 15 min; 60 °C for 10 min; 50 °C for 10 min; 40 °C for 10 min; and 25 °C for 30 min; and step 3: mixing the reaction system I and the reaction system II in an equimolar manner after the reaction procedure to obtain the ChIP double strand adapter mixture.

10. The method according to claim 1, wherein each of the steps (A3) and (B3) further comprises steps of centrifugation and washing after the second incubation, wherein the centrifugation is performed at 600 g for 3 min, and the washing is performed with a chitag enzyme incubation buffer.

11. The method according to claim 1, wherein in the steps (A5) and (B5), the reaction reagent is directly added to a cell precipitation obtained with the centrifugation in the step (A4), wherein the reaction reagent is a chitag enzyme breaking buffer, the chitag enzyme breaking buffer is obtained by adding 10 mM of $MgCl_2$ to a chitag enzyme incubation buffer.

12. The method according to claim 1, wherein in the steps (A5) and (B5), the fourth incubation is performed at 37 °C for 60 min, wherein a centrifugation at 300 g for 3 min after the fourth incubation is performed, and the Tn5 transposase is added and reacted at 37 °C with 500 rpm for 30 min.

13. The method according to claim 1, wherein in each of the steps (A5) and (B5), the PrimerA, an ATAC-Tn5-PrimerB and an ATAC-Tn5-PrimerC are added while adding the Tn5 transposase, the PrimerA is the single strand DNA shown in SEQ ID NO: 1 modified with a phosphate group at the 5' end, the ATAC-Tn5-PrimerB is a mixture of four single strand DNAs as shown in SEQ ID NO: 10, SEQ ID NO: 11, SEQ ID NO: 12 and SEQ ID NO: 13 and the ATAC-Tn5-PrimerC is a mixture of four single strand DNAs as shown in SEQ ID NO: 14, SEQ ID NO: 15, SEQ ID NO: 16 and SEQ ID NO: 17.

14. The method according to claim 13, wherein in the steps (A5) and (B5), the Tn5 transposase is added in a form of an ATAC transposable reagent mixture, and per 25 μl of the ATAC transposable reagent mixture comprises 5 μl of 5×TAG buffer, 16 μl of PBS with 1% BSA, and 4 μl of a Tn5 adapter complex, wherein the Tn5 adapter complex is obtained by evenly mixing the Tn5 transposase and a Tn5 double strand adapter mixture at a molar ratio of 1:1 and an incubation incubating at 25 °C for 1 h, wherein a final concentration of the Tn5 transposase in the Tn5 adapter complex is 0.875U/μl, and the Tn5 double strand adapter mixture comprises the PrimerA, the ATAC-Tn5-PrimerB and the ATAC-Tn5-PrimerC, wherein the Tn5 double strand adapter mixture is prepared according to a method comprising the following steps:

step 1, preparing the following reaction systems by:

for a reaction system I, mixing the PrimerA and the ATAC-Tn5-PrimerB in an equimolar manner, and for a reaction system II, mixing the PrimerA and the ATAC-Tn5-PrimerC in an equimolar manner, step 2, subjecting the reaction system I and the reaction system II individually to the following reaction procedure of 75 °C for 15 min; 60 °C for 10 min; 50 °C for 10 min; 40 °C for 10 min; and 25 C for 30 min; and step 3: mixing the reaction system I and the reaction system II in an equimolar manner after the reaction procedure to obtain the Tn5 double strand adapter mixture.

15. The method according to claim 2, wherein in the step (A6), primers for the amplification within the droplet comprise a Tn Primer and a 183+C Primer, wherein the Tn Primer is a single strand DNA as shown in SEQ ID NO: 18, and the 183+C Primer is a single strand DNA as shown in SEQ ID NO: 19.

16. The method according to claim 2, wherein in the step (A7), primers for the amplification comprise the Tn Primer and a 183-pho Primer, wherein the Tn Primer is the single strand DNA as shown in SEQ ID NO: 18, and the 183-pho Primer is a single strand DNA modified with a phosphate group at the 5' end as shown in SEQ ID NO: 20.

17. The method according to claim 2, wherein in the step (A7), the purification is performed by adding 1.2 volumes of magnetic beads to a product of the amplification.

18. The method according to claim 2, wherein in the step (B6), primers for the amplification comprise a Bulk-N5 Primer and a 183+C-pho Primer, wherein the Bulk-N5 Primer is a single strand DNA as shown in SEQ ID NO: 22, and the 183+C-pho Primer is a single strand DNA modified with a phosphate group at the 5' end as shown in SEQ ID NO: 23.

19. The method according to claim 2, wherein each of the steps (A8) and (B7) further comprises a cyclization before the enzyme digestion, the cyclization is performed with a 153+181 Splint oligo, wherein the 153+181 Splint oligo is a single strand DNA as shown in SEQ ID NO: 21.

20. A method for any one of:

(C1) researching cell population heterogeneity related to a development and/or a disease;

(C2) drawing a cell atlas;

(C3) analyzing tumor cells with different clinical features; or (C4) studying an evolution and/or metastasis of a tumor cell clinically, wherein the method comprises the following steps:

utilizing a ChiTag transposase and a Tn5 transposase to respectively embed different adapter sequences in a cell; and performing a co-analysis for information of an accessible-chromatin region and a target-protein binding sequence at the cellular level, wherein the method is a method A or a method B, wherein the method A is a method for multi-dimensional analysis of single-cell epigenomics, comprising the following steps:

(A1) changing the permeability of a cell to be tested;

(A2) adding an antibody corresponding to the target protein to the cell after the treatment of the step (A1) for a first incubation;

(A3) adding a secondary antibody to the cell after the treatment of the step (A2) for a second incubation;

(A4) adding the ChiTag transposase to the cell after the treatment of the step (A3) for a third incubation; and (A5) adding a reaction reagent to the cell after the treatment of the step (A4) for a fourth incubation, and adding the Tn5 transposase after the fourth incubation, the method B is a method for multi-dimensional analysis of multi-cell epigenomics, comprising the following steps:

(B1) changing the permeability of a cell to be tested;

(B2) adding an antibody corresponding to the target protein to the cell after the treatment of the step (B1) for a first incubation;

(B3) adding a secondary antibody to the cell after the treatment of the step (B2) for a second incubation;

(B4) adding the ChiTag transposase to the cell after the treatment of the step (B3) for a third incubation; and (B5) adding a reaction reagent to the cell after the treatment of the step (B4) for a fourth incubation, and adding the Tn5 transposase after the fourth incubation.

* * * * *

SEQUENCE LISTING

```
<160> NUMBER OF SEQ ID NOS: 23

<210> SEQ ID NO 1
<211> LENGTH: 19
<212> TYPE: DNA
<213> ORGANISM: Artificial sequence
<220> FEATURE:
<223> OTHER INFORMATION: Synthesized sequence

<400> SEQUENCE: 1

ctgtctctta tacacatct                                              19


<210> SEQ ID NO 2
<211> LENGTH: 56
<212> TYPE: DNA
<213> ORGANISM: Artificial sequence
<220> FEATURE:
<223> OTHER INFORMATION: Synthesized sequence

<400> SEQUENCE: 2

tcgtcggcag cgtcaggcga aggcgatcga ggacggcaga tgtgtataag agacag      56


<210> SEQ ID NO 3
<211> LENGTH: 56
<212> TYPE: DNA
<213> ORGANISM: Artificial sequence
<220> FEATURE:
<223> OTHER INFORMATION: Synthesized sequence

<400> SEQUENCE: 3

tcgtcggcag cgtctaatct tagcgatcga ggacggcaga tgtgtataag agacag      56
```

<210> SEQ ID NO 4
<211> LENGTH: 56
<212> TYPE: DNA
<213> ORGANISM: Artificial sequence
<220> FEATURE:
<223> OTHER INFORMATION: Synthesized sequence

<400> SEQUENCE: 4
tcgtcggcag cgtccaggac gtgcgatcga ggacggcaga tgtgtataag agacag 56

<210> SEQ ID NO 5
<211> LENGTH: 56
<212> TYPE: DNA
<213> ORGANISM: Artificial sequence
<220> FEATURE:
<223> OTHER INFORMATION: Synthesized sequence

<400> SEQUENCE: 5
tcgtcggcag cgtcgtactg acgcgatcga ggacggcaga tgtgtataag agacag 56

<210> SEQ ID NO 6
<211> LENGTH: 59
<212> TYPE: DNA
<213> ORGANISM: Artificial sequence
<220> FEATURE:
<223> OTHER INFORMATION: Synthesized sequence

<400> SEQUENCE: 6
gtctcgtggg ctcggaatct atcaacaccg tctccgcctc agatgtgtat aagagacag 59

<210> SEQ ID NO 7
<211> LENGTH: 59
<212> TYPE: DNA
<213> ORGANISM: Artificial sequence
<220> FEATURE:
<223> OTHER INFORMATION: Synthesized sequence

<400> SEQUENCE: 7
gtctcgtggg ctcggaccag gaaggcaccg tctccgcctc agatgtgtat aagagacag 59

<210> SEQ ID NO 8
<211> LENGTH: 59
<212> TYPE: DNA
<213> ORGANISM: Artificial sequence
<220> FEATURE:
<223> OTHER INFORMATION: Synthesized sequence

<400> SEQUENCE: 8
gtctcgtggg ctcgggagag atattcaccg tctccgcctc agatgtgtat aagagacag 59

<210> SEQ ID NO 9
<211> LENGTH: 59
<212> TYPE: DNA
<213> ORGANISM: Artificial sequence
<220> FEATURE:
<223> OTHER INFORMATION: Synthesized sequence

<400> SEQUENCE: 9
gtctcgtggg ctcgggggaa acatgcaccg tctccgcctc agatgtgtat aagagacag 59

<210> SEQ ID NO 10
<211> LENGTH: 56
<212> TYPE: DNA
<213> ORGANISM: Artificial sequence
<220> FEATURE:
<223> OTHER INFORMATION: Synthesized sequence

<400> SEQUENCE: 10
tcgtcggcag cgtctatagc ctgcgatcga ggacggcaga tgtgtataag agacag 56

<210> SEQ ID NO 11
<211> LENGTH: 56
<212> TYPE: DNA
<213> ORGANISM: Artificial sequence
<220> FEATURE:
<223> OTHER INFORMATION: Synthesized sequence

<400> SEQUENCE: 11
tcgtcggcag cgtcatagag gcgcgatcga ggacggcaga tgtgtataag agacag 56

<210> SEQ ID NO 12
<211> LENGTH: 56
<212> TYPE: DNA
<213> ORGANISM: Artificial sequence
<220> FEATURE:
<223> OTHER INFORMATION: Synthesized sequence

<400> SEQUENCE: 12
tcgtcggcag cgtccctatc ctgcgatcga ggacggcaga tgtgtataag agacag 56

<210> SEQ ID NO 13
<211> LENGTH: 56
<212> TYPE: DNA
<213> ORGANISM: Artificial sequence
<220> FEATURE:
<223> OTHER INFORMATION: Synthesized sequence

<400> SEQUENCE: 13
tcgtcggcag cgtcggctct gagcgatcga ggacggcaga tgtgtataag agacag 56

<210> SEQ ID NO 14
<211> LENGTH: 59
<212> TYPE: DNA
<213> ORGANISM: Artificial sequence
<220> FEATURE:
<223> OTHER INFORMATION: Synthesized sequence

<400> SEQUENCE: 14
gtctcgtggg ctcggattta tgacacaccg tctccgcctc agatgtgtat aagagacag 59

<210> SEQ ID NO 15
<211> LENGTH: 59
<212> TYPE: DNA
<213> ORGANISM: Artificial sequence
<220> FEATURE:
<223> OTHER INFORMATION: Synthesized sequence

<400> SEQUENCE: 15
gtctcgtggg ctcggcctta attaacaccg tctccgcctc agatgtgtat aagagacag 59

<210> SEQ ID NO 16
<211> LENGTH: 59
<212> TYPE: DNA
<213> ORGANISM: Artificial sequence
<220> FEATURE:
<223> OTHER INFORMATION: Synthesized sequence

<400> SEQUENCE: 16
gtctcgtggg ctcggtcagt gagtccaccg tctccgcctc agatgtgtat aagagacag 59

<210> SEQ ID NO 17

<211> LENGTH: 59
<212> TYPE: DNA
<213> ORGANISM: Artificial sequence
<220> FEATURE:
<223> OTHER INFORMATION: Synthesized sequence

<400> SEQUENCE: 17
gtctcgtggg ctcggactgc cttatcaccg tctccgcctc agatgtgtat aagagacag 59

<210> SEQ ID NO 18
<211> LENGTH: 18
<212> TYPE: DNA
<213> ORGANISM: Artificial sequence
<220> FEATURE:
<223> OTHER INFORMATION: Synthesized sequence

<400> SEQUENCE: 18
cgtagccatg tcgttctg 18

<210> SEQ ID NO 19
<211> LENGTH: 37
<212> TYPE: DNA
<213> ORGANISM: Artificial sequence
<220> FEATURE:
<223> OTHER INFORMATION: Synthesized sequence

<400> SEQUENCE: 19
gagacgttct cgactcagca gagtctcgtg ggctcgg 37

<210> SEQ ID NO 20
<211> LENGTH: 22
<212> TYPE: DNA
<213> ORGANISM: Artificial sequence
<220> FEATURE:
<223> OTHER INFORMATION: Synthesized sequence

<400> SEQUENCE: 20
gagacgttct cgactcagca ga 22

<210> SEQ ID NO 21
<211> LENGTH: 24
<212> TYPE: DNA
<213> ORGANISM: Artificial sequence
<220> FEATURE:
<223> OTHER INFORMATION: Synthesized sequence

<400> SEQUENCE: 21
cgagaacgtc tccgtagcca tgtc 24

<210> SEQ ID NO 22
<211> LENGTH: 34
<212> TYPE: DNA
<213> ORGANISM: Artificial sequence
<220> FEATURE:
<223> OTHER INFORMATION: Synthesized sequence

<400> SEQUENCE: 22
cgtagccatg tcgttctgcg tcgtcggcag cgtc 34

<210> SEQ ID NO 23
<211> LENGTH: 37
<212> TYPE: DNA
<213> ORGANISM: Artificial sequence
<220> FEATURE:
<223> OTHER INFORMATION: Synthesized sequence -continued

<400> SEQUENCE: 23
gagacgttct cgactcagca gagtctcgtg ggctcgg 37